(12) United States Patent
Fredriksson et al.

(10) Patent No.: US 10,781,473 B2
(45) Date of Patent: Sep. 22, 2020

(54) METHOD FOR GENERATING PROXIMITY PROBES

(71) Applicant: Olink Proteomics AB, Uppsala (SE)

(72) Inventors: Johan Erik Simon Fredriksson, Bromma (SE); Klas Martin Lundberg, Uppsala (SE)

(73) Assignee: OLINK PROTEOMICS AB, Uppsala (SE)

( * ) Notice: Subject to any disclaimer, the term of this patent is extended or adjusted under 35 U.S.C. 154(b) by 0 days.

(21) Appl. No.: 15/769,904

(22) PCT Filed: Oct. 21, 2016

(86) PCT No.: PCT/EP2016/075360
§ 371 (c)(1),
(2) Date: Apr. 20, 2018

(87) PCT Pub. No.: WO2017/068116
PCT Pub. Date: Apr. 27, 2017

(65) Prior Publication Data
US 2018/0312901 A1    Nov. 1, 2018

(30) Foreign Application Priority Data
Oct. 21, 2015 (GB) .................................. 1518655.4

(51) Int. Cl.
*C12Q 1/68* (2018.01)
*C12Q 1/6804* (2018.01)
*G01N 33/53* (2006.01)
*C12Q 1/6818* (2018.01)

(52) U.S. Cl.
CPC ......... *C12Q 1/6804* (2013.01); *C12Q 1/6818* (2013.01); *G01N 33/53* (2013.01)

(58) Field of Classification Search
None
See application file for complete search history.

(56) References Cited

U.S. PATENT DOCUMENTS

| 4,336,173 | A | 6/1982 | Ugelstad |
| 4,683,195 | A | 7/1987 | Mullis et al. |
| 4,683,202 | A | 7/1987 | Mullis et al. |
| 4,800,159 | A | 1/1989 | Mullis et al. |
| 4,965,188 | A | 10/1990 | Mullis et al. |
| 5,449,603 | A | 9/1995 | Nielson et al. |
| 5,534,407 | A | 7/1996 | Tabor et al. |
| 5,635,602 | A | 6/1997 | Cantor et al. |
| 5,721,099 | A | 2/1998 | Still et al. |
| 5,733,523 | A | 3/1998 | Kuijpers et al. |
| 5,741,713 | A | 4/1998 | Brown et al. |
| 5,773,258 | A | 6/1998 | Birch et al. |
| 5,849,878 | A | 12/1998 | Cantor et al. |
| 5,989,823 | A | 11/1999 | Jayasena et al. |
| 6,117,635 | A | 9/2000 | Nazarenko et al. |
| 6,183,960 | B1 | 2/2001 | Lizardi |
| 6,248,526 | B1 | 6/2001 | Weimer |
| 6,326,145 | B1 | 12/2001 | Whitcombe et al. |
| 6,511,809 | B2 | 1/2003 | Baez et al. |
| 6,558,928 | B1 | 5/2003 | Landegren |
| 7,306,904 | B2 | 12/2007 | Landegren et al. |
| 2002/0051986 | A1 | 5/2002 | Baez et al. |
| 2003/0152932 | A1 | 8/2003 | Kumar et al. |
| 2005/0009050 | A1 | 1/2005 | Nadeau et al. |
| 2005/0221349 | A1 | 10/2005 | Wilson et al. |
| 2005/0282158 | A1 | 12/2005 | Landegren et al. |
| 2008/0090238 | A1 | 4/2008 | Yang et al. |
| 2008/0131883 | A1 | 6/2008 | Adams et al. |
| 2009/0061426 | A1 | 3/2009 | Belyaev et al. |
| 2009/0162840 | A1 | 6/2009 | Fredriksson et al. |
| 2010/0021890 | A1 | 1/2010 | Schallmeiner |
| 2010/0159455 | A1 | 6/2010 | Landsman et al. |
| 2011/0053782 | A1 | 3/2011 | Hirao et al. |
| 2012/0082988 | A1 | 4/2012 | Adams et al. |
| 2018/0100189 | A1 | 4/2018 | Fredriksson et al. |

FOREIGN PATENT DOCUMENTS

| EP | 1066414 | A1 | 1/2001 |
| EP | 1842226 | A2 | 10/2007 |
| EP | 2275538 | A1 | 1/2011 |
| JP | 2003-524419 | A | 8/2003 |
| JP | 2014-504880 | A | 2/2014 |
| WO | 93/06240 | A1 | 4/1993 |
| WO | 95/05399 | A1 | 2/1995 |

(Continued)

OTHER PUBLICATIONS

Di Giusto, Daniel A, et al., Proximity extension of circular DNA aptamers with real-time protein detection, Nucleic Acids Research, vol. 33, No. 6, pp. 1-7 (published online Apr. 7, 2005).
Fredriksson, Simon et al., Protein detection using proximity-dependent DNA ligation assays, Nature Biotechnology, vol. 20, pp. 473-477 (May 2002).
Gullberg, Mats et al., Cytokine detection by antibody-based proximity ligation, PNAS, vol. 101, No. 22, pp. 3420-8424 (Jun. 1, 2004).
Gustafsdottir, Sigrun M. et al., Proximity ligation assays for sensitive and specific protein analyses, Analytical Biochemistry, vol. 345, pp. 2-9 (2005).
Kaboev, O. K. et al., PCR hot start using primers with the structure of molecular beacons (hairpin-like structure), Nucleic Acids Research, vol. 28, No. 21, pp. 1-2 (2000).

(Continued)

*Primary Examiner* — James Martinell
(74) *Attorney, Agent, or Firm* — Porter Wright Morris & Arthur LLP

(57) ABSTRACT

The present invention provides a plurality of pairs of proximity probes, each pair being capable of binding to a different target analyte, wherein the first and second proximity probes of each pair of probes comprise universal oligonucleotides conjugated to their analyte binding moieties, and hybridised to the universal oligonucleotides are different tag oligonucleotides comprising universal complement domains common to all tag oligonucleotides and unique domains unique to each tag oligonucleotide, as well as methods for their production.

20 Claims, 5 Drawing Sheets

Specification includes a Sequence Listing.

(56) References Cited

FOREIGN PATENT DOCUMENTS

| | | | |
|---|---|---|---|
| WO | 99/49079 | A1 | 9/1999 |
| WO | 01/61037 | A1 | 8/2001 |
| WO | 03012119 | A2 | 2/2003 |
| WO | 03044231 | A1 | 5/2003 |
| WO | 2004061132 | A1 | 7/2004 |
| WO | 2004094456 | A2 | 11/2004 |
| WO | 2005123963 | A2 | 12/2005 |
| WO | 2006137932 | A2 | 12/2006 |
| WO | 2007/005649 | A2 | 1/2007 |
| WO | 2007/044864 | A2 | 4/2007 |
| WO | 2007/107743 | A2 | 9/2007 |
| WO | 2009/012220 | A2 | 1/2009 |
| WO | 2009/021031 | A2 | 2/2009 |
| WO | 2009/045906 | A2 | 4/2009 |
| WO | 2009123216 | A1 | 10/2009 |
| WO | 2011100561 | A1 | 8/2011 |
| WO | 2012/007511 | A1 | 1/2012 |
| WO | 2012/049316 | A1 | 4/2012 |
| WO | 2012057689 | A1 | 5/2012 |
| WO | 2012071428 | A2 | 5/2012 |
| WO | 2012104261 | A1 | 8/2012 |
| WO | 2012152942 | A1 | 11/2012 |
| WO | 2013/113699 | A2 | 8/2013 |
| WO | 2015/118029 | A1 | 8/2015 |

OTHER PUBLICATIONS

Landegren Ulf et al., Padlock and proximity probes for in situ and array-based analyses: tools for the post-genomic era, Comparative and Functional Genomics, vol. 4, No. 5, pp. 525-530 (2003).
Landegren Ulf et al., Molecular tools for a molecular medicine: analyzing genes, transcripts and proteins using padlock and proximity probes, J. Mol. Recogmt., vol. 17, No. 3, pp. 194-197 (2004).
Lee, Linda G. et al., Allelic discrimination by nick-translation PCR with fluorogenic probes, Nucleic Acids Research, vol. 21, No. 16, pp. 3761-3766 (1993).
Lundberg, Kelly S., High-fidelity amplification using a thermostable DNA polymerase isolated from Pyrococcus furiosus, Gene., vol. 108, pp. 1-6 (1991).
Lundberg, Martin et al., Homogeneous antibody-based proximity extension assays provide sensitive and specific detection of low-abundant proteins in human blood, Nucleic Acids Research, vol. 39, No. 15, pp. 1-8 (2011).
Nilsson, Mats et al., Real-time monitoring of rolling-circle amplification using a modified molecular beacon design, Nucleic Acids Research, vol. 30, No. 14, pp. 1-7 (2002).
PROSEEK Mutiplex user manual, Olink Bioscience, vol. 1.4, pp. 1-20 (2014).
Schallmeiner, Edith et al., Sensitive protein detection via triple-binder proximity ligation assays, Nature Methods, vol. 4, No. 2, pp. 135-137 (Feb. 2007).
Schwitzer, Barry et al., Immunoassays with rolling circle DNA amplification: A versatile platform for ultrasensitive antigen detection, PNAS, vol. 97, No. 18, pp. 10113-10119 (Aug. 29, 2000).
Söderberg, Ola et al., Direct observation of individual endogenous protein complexes in situ by proximity ligation, Nature Methods, vol. 3, No. 12, pp. 995-1000 (Dec. 2006).
Söderberg, Ola et al., Characterizing proteins and their interactions in cells and tissues using the in situ proximity ligation assay, Methods, vol. 45, No. 3, pp. 227-232 (2008).
Tang, Na et al., The New Technique for Protein Analysis: Proximity Ligation Assay and Its Application, China Biotechnology, vol. 29, No. 8, pp. 113-118 (2009).
Tyagi, Sanjay et al., Molecular Beacons: Probes that Fluoresce upon Hybridization, Nature Biotechnology, vol. 14, pp. 303-308 (Mar. 1996).
Weibrecht, Irene et al., Proximity ligation assays: a recent addition to the proteomics toolbox, Expert Rev. Proteomics, vol. 7, No. 3, pp. 401-409 (2010).
Whitcombe, David et al., Detection of PCR products using self-probing amplicons and fluorescence, Nature Biotechnology, vol. 17, pp. 804-807 (Aug. 1999).
Yan, Junhong et al., A Universal Approach to Prepare Reagents for DNA-Assisted Protein Analysis, PLOS ONE, vol. 9, Issue 9, e108061, pp. 1-8 (Sep. 2014).
Office Action dated Jun. 30, 2020 from corresponding Japanese Application No. 2018-520544 with English Translation.

Functional domains

Analyte binding domains

Universal complement domains

Unique domains

Tag oligonucleotides

Universal oligonucleotide

Analyte binding domains

Universal oligonucleotide

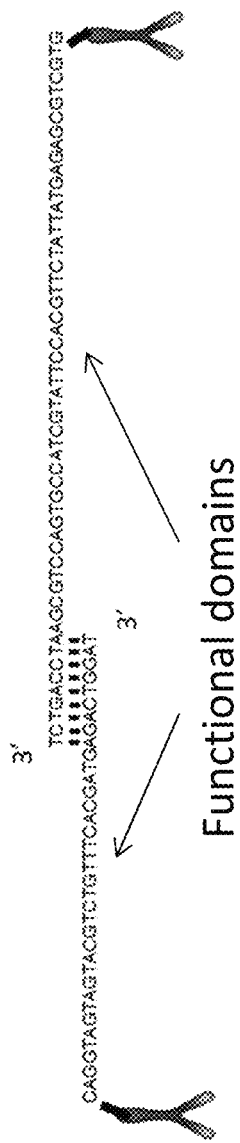
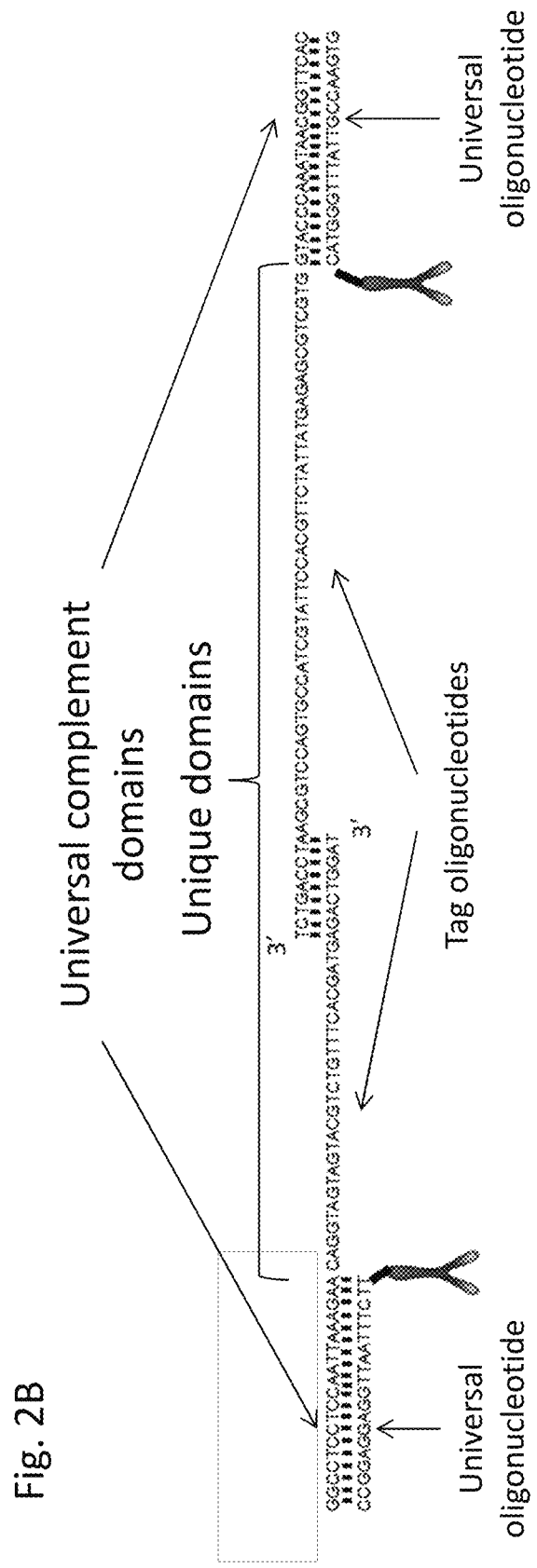
Fig. 2A
Fig. 2B

Universal conjugates

Probe pair #1

Probe pair #2

Probe pair #3

Direct conjugation

Probe pair #4

SEQUENCE LISTING

<160> NUMBER OF SEQ ID NOS: 24

<210> SEQ ID NO 1
<211> LENGTH: 20
<212> TYPE: DNA
<213> ORGANISM: Artificial Sequence
<220> FEATURE:
<223> OTHER INFORMATION: Universal oligo 1

<400> SEQUENCE: 1
ttctttaatt ggaggaggcc                                        20

```
<210> SEQ ID NO 2
<211> LENGTH: 20
<212> TYPE: DNA
<213> ORGANISM: Artificial Sequence
<220> FEATURE:
<223> OTHER INFORMATION: Universal oligo 2

<400> SEQUENCE: 2
catgggttta ttgccaagtg                                              20

<210> SEQ ID NO 3
<211> LENGTH: 20
<212> TYPE: DNA
<213> ORGANISM: Artificial Sequence
<220> FEATURE:
<223> OTHER INFORMATION: Universal complement domain 1'

<400> SEQUENCE: 3
ggcctcctcc aattaaagaa                                              20

<210> SEQ ID NO 4
<211> LENGTH: 20
<212> TYPE: DNA
<213> ORGANISM: Artificial Sequence
<220> FEATURE:
<223> OTHER INFORMATION: Universal complement domain 2'

<400> SEQUENCE: 4
cacttggcaa taaacccatg                                              20

<210> SEQ ID NO 5
<211> LENGTH: 57
<212> TYPE: DNA
<213> ORGANISM: Artificial Sequence
<220> FEATURE:
<223> OTHER INFORMATION: First tag I

<400> SEQUENCE: 5
ggcctcctcc aattaaagaa caggtagtag tacgtctgtt tcacgatgag actggat     57

<210> SEQ ID NO 6
<211> LENGTH: 57
<212> TYPE: DNA
<213> ORGANISM: Artificial Sequence
<220> FEATURE:
<223> OTHER INFORMATION: First tag II

<400> SEQUENCE: 6
ggcctcctcc aattaaagaa ggcctcctcc aattaaagaa tcacgatgag actggat     57

<210> SEQ ID NO 7
<211> LENGTH: 57
<212> TYPE: DNA
<213> ORGANISM: Artificial sequence
<220> FEATURE:
<223> OTHER INFORMATION: First tag III

<400> SEQUENCE: 7
ggcctcctcc aattaaagaa ggatcactcc aactagacta tcacgatgag actggat     57

<210> SEQ ID NO 8
<211> LENGTH: 57
<212> TYPE: DNA
<213> ORGANISM: Artificial Sequence
<220> FEATURE:
```

<223> OTHER INFORMATION: First tag IV

<400> SEQUENCE: 8
ggcctcctcc aattaaagaa agagtccact tcccataatg tcacgatgag actggat    57

<210> SEQ ID NO 9
<211> LENGTH: 57
<212> TYPE: DNA
<213> ORGANISM: Artificial Sequence
<220> FEATURE:
<223> OTHER INFORMATION: First tag V

<400> SEQUENCE: 9
ggcctcctcc aattaaagaa ctacgactag gagatagatg tcacgatgag actggat    57

<210> SEQ ID NO 10
<211> LENGTH: 57
<212> TYPE: DNA
<213> ORGANISM: Artificial sequence
<220> FEATURE:
<223> OTHER INFORMATION: First tag VI

<400> SEQUENCE: 10
ggcctcctcc aattaaagaa ccctcgtaca caatggataa tcacgatgag actggat    57

<210> SEQ ID NO 11
<211> LENGTH: 57
<212> TYPE: DNA
<213> ORGANISM: Artificial sequence
<220> FEATURE:
<223> OTHER INFORMATION: First tag VII

<400> SEQUENCE: 11
ggcctcctcc aattaaagaa gactcccact tcttgtaatg tcacgatgag actggat    57

<210> SEQ ID NO 12
<211> LENGTH: 57
<212> TYPE: DNA
<213> ORGANISM: Artificial sequence
<220> FEATURE:
<223> OTHER INFORMATION: First tag VIII

<400> SEQUENCE: 12
ggcctcctcc aattaaagaa cagacggtca aatcctctaa tcacgatgag actggat    57

<210> SEQ ID NO 13
<211> LENGTH: 57
<212> TYPE: DNA
<213> ORGANISM: Artificial sequence
<220> FEATURE:
<223> OTHER INFORMATION: First tag IX

<400> SEQUENCE: 13
ggcctcctcc aattaaagaa gaggtagctc actccacatg tcacgatgag actggat    57

<210> SEQ ID NO 14
<211> LENGTH: 57
<212> TYPE: DNA
<213> ORGANISM: Artificial sequence
<220> FEATURE:
<223> OTHER INFORMATION: First tag X

<400> SEQUENCE: 14
ggcctcctcc aattaaagaa gtctaagatc ctatcacacg tcacgatgag actggat    57

```
<210> SEQ ID NO 15
<211> LENGTH: 76
<212> TYPE: DNA
<213> ORGANISM: Artificial sequence
<220> FEATURE:
<223> OTHER INFORMATION: Second tag I

<400> SEQUENCE: 15
cacttggcaa taaacccatg gtgctgcgag agtattatct tgcaccttat gctaccgtga      60
cctgcgaatc cagtct                                                     76

<210> SEQ ID NO 16
<211> LENGTH: 76
<212> TYPE: DNA
<213> ORGANISM: Artificial sequence
<220> FEATURE:
<223> OTHER INFORMATION: Second tag II

<400> SEQUENCE: 16
cacttggcaa taaacccatg gtgaaccgtt atttgggtac tgcaccttat gctaccgtga      60
cctgcgaatc cagtct                                                     76

<210> SEQ ID NO 17
<211> LENGTH: 76
<212> TYPE: DNA
<213> ORGANISM: Artificial sequence
<220> FEATURE:
<223> OTHER INFORMATION: Second tag III

<400> SEQUENCE: 17
cacttggcaa taaacccatg gtgacagtgg cagatataac tgcaccttat gctaccgtga      60
cctgcgaatc cagtct                                                     76

<210> SEQ ID NO 18
<211> LENGTH: 76
<212> TYPE: DNA
<213> ORGANISM: Artificial sequence
<220> FEATURE:
<223> OTHER INFORMATION: Second tag IV

<400> SEQUENCE: 18
cacttggcaa taaacccatg gaactatgct gacagtaccg tgcaccttat gctaccgtga      60
cctgcgaatc cagtct                                                     76

<210> SEQ ID NO 19
<211> LENGTH: 76
<212> TYPE: DNA
<213> ORGANISM: Artificial sequence
<220> FEATURE:
<223> OTHER INFORMATION: Second tag V

<400> SEQUENCE: 19
cacttggcaa taaacccatg gcgagcgtac tatacataac tgcaccttat gctaccgtga      60
cctgcgaatc cagtct                                                     76

<210> SEQ ID NO 20
<211> LENGTH: 76
<212> TYPE: DNA
<213> ORGANISM: Artificial sequence
<220> FEATURE:
<223> OTHER INFORMATION: Second tag VI

<400> SEQUENCE: 20
```

```
cacttggcaa taaacccatg gcaggcagat cgacctagtt tgcaccttat gctaccgtga     60
cctgcgaatc cagtct                                                     76

<210> SEQ ID NO 21
<211> LENGTH: 76
<212> TYPE: DNA
<213> ORGANISM: Artificial sequence
<220> FEATURE:
<223> OTHER INFORMATION: Second tag VII

<400> SEQUENCE: 21
cacttggcaa taaacccatg gagtttatac tacagtgccg tgcaccttat gctaccgtga     60
cctgcgaatc cagtct                                                     76

<210> SEQ ID NO 22
<211> LENGTH: 76
<212> TYPE: DNA
<213> ORGANISM: Artificial sequence
<220> FEATURE:
<223> OTHER INFORMATION: Second tag VIII

<400> SEQUENCE: 22
cacttggcaa taaacccatg gttgccgtac tagggatact tgcaccttat gctaccgtga     60
cctgcgaatc cagtct                                                     76

<210> SEQ ID NO 23
<211> LENGTH: 76
<212> TYPE: DNA
<213> ORGANISM: Artificial sequence
<220> FEATURE:
<223> OTHER INFORMATION: Second tag IX

<400> SEQUENCE: 23
cacttggcaa taaacccatg gcctgcgaat tagcggacat tgcaccttat gctaccgtga     60
cctgcgaatc cagtct                                                     76

<210> SEQ ID NO 24
<211> LENGTH: 76
<212> TYPE: DNA
<213> ORGANISM: Artificial sequence
<220> FEATURE:
<223> OTHER INFORMATION: Second tag X

<400> SEQUENCE: 24
cacttggcaa taaacccatg gttgtttagt aagtggcacc tgcaccttat gctaccgtga     60
cctgcgaatc cagtct                                                     76
```

METHOD FOR GENERATING PROXIMITY PROBES

FIELD OF THE INVENTION

The Sequence Listing submitted herewith, entitled "123673-01-sequence-listing_ST25.txt", created April 18, 2018 and having a size of 5501 bytes, is incorporated herein by reference.

The present invention relates to methods for the manufacture of probes (proximity probes) for use in proximity probe based detection assays for an analyte in a sample. In particular, the present invention relates to an improved method for producing a plurality of proximity probe pairs having different target analyte binding specificities, and comprising different nucleic acid domains.

BACKGROUND OF THE INVENTION

Proximity probes are generally used in pairs, e.g. first and second proximity probes, and each proximity probe in a pair generally comprises an analyte-binding domain with specificity to the target analyte, and a functional domain, e.g. a nucleic acid domain coupled thereto. However, versions of proximity assays exist in which more than two, e.g. three, proximity probes can be used in combination. The analyte-binding domain can be for example a nucleic acid "aptamer" (Fredriksson et al (2002) Nat Biotech 20:473-477) or can be proteinaceous, such as a monoclonal or polyclonal antibody (Gullberg et al (2004) Proc Natl Acad Sci USA 101:8420-8424). The respective analyte-binding domains of each proximity probe pair may have specificity for different binding sites on the analyte, which analyte may consist of a single molecule or a complex of interacting molecules, or may have identical specificities, for example in the event that the target analyte exists as a multimer.

A proximity assay relies on the principle of "proximity probing", wherein an analyte is detected by the binding of multiple (i.e. two or more, generally two or three) probes, which when brought into proximity by binding to the analyte (hence "proximity probes") allow a signal to be generated. Generation of the signal in a proximity assay involves an interaction between the nucleic acid domains and/or a further functional moiety which is added to a sample or carried by the other probe(s). When a pair (or set) of proximity probes come into close proximity with each other, which will primarily occur when both (or all) are bound to their respective sites on the same analyte molecule, or different analyte molecules in a complex, the functional domains (e.g. nucleic acid domains) are able to interact, directly or indirectly, to generate a detectable signal (i.e. a nucleic acid sequence which was not previously present in the sample) that can be detected to indicate presence of a target antigen in a sample. Thus signal generation is dependent on an interaction between the probes (more particularly by the nucleic acid or other functional moieties/domains carried by them) and typically requires the formation of one or more nucleic acid duplexes e.g. by the direct or indirect interaction of the nucleic acid domains, which enables a ligation reaction (either of nucleic acid domains to each other, or wherein the nucleic acid domain(s) template the ligation of one or more separately added oligonucleotides) and/or extension reaction (e.g. of at least one of the nucleic acid domains), thereby to generate a detectable signal. A signal hence only occurs when both (or all) the necessary probes have bound to the analyte, thereby lending improved specificity to the detection system. The concept of proximity probing has been developed in recent years and many assays based on this principle are now well known in the art, for instance proximity probe based detection assays include proximity extension assays (PEA), proximity ligation assays (PLA) (U.S. Pat. No. 6,878,515, WO 01/61037), in situ PLA (WO9949079) (which is a PLA used to detect molecules in a localised manner in situ in a cell or tissue sample, in which a circular nucleic acid molecule is formed by ligation of one or more (typically 2) added oligonucleotides templated by one or more nucleic acid domains, wherein the circular molecule is amplified by rolling circle amplification primed by a nucleic acid domain, thereby to localise the amplification product to the proximity probe and hence to the analyte), and proximity HCR PCT/EP2015/052340.

The manufacture of probes for use in proximity-based detection assays requires the conjugation (i.e. coupling or linking) of a nucleic acid domain (or moiety) to an analyte binding domain. The nucleic acid domain (i.e. the functional domain, which interacts with another nucleic acid domain or nucleic acid molecule in the sample to produce a detectable signal) is typically conjugated (e.g. by covalent linkage) to an analyte binding domain to form a proximity probe. However, since nucleic acid domains (functional domains) are typically attached directly to their respective analyte binding domains, the manufacture of each proximity probe comprising particular nucleic acid and analyte binding domains typically requires the activation of a nucleic acid molecule and its subsequent conjugation to its respective analyte binding domain. Thus, a new oligonucleotide molecule will be activated and conjugated to the required analyte binding domain whenever a new proximity probe is required. This increases the time and cost associated with generating new reagents for use in proximity-based detection assays, and is a significant factor holding back the expansion of high-throughput (e.g. multiplexed) proximity detection assays.

Furthermore, the efficiency of activation of oligonucleotides (and thus the efficiency of conjugation of a nucleic acid domain to its analyte binding domain) is known to vary. As an oligonucleotide is independently activated and conjugated to its respective analyte binding domain each time a probe is manufactured, it can be difficult to ensure that different proximity probes (e.g. analyte binding domains conjugated to different nucleic acid domains) comprise similar levels of the oligonucleotide. The efficiency of detection of different target analyte in proximity detection assays will thus be variable, hindering any comparisons from being drawn between the different levels of analytes in a sample.

Consistency between separate batches of probes produced via this method is also difficult to achieve, for similar reasons, thus affecting the reproducibility of proximity detection assays and limiting the size of studies that can be performed Current manufacturing methods also fail to provide a straightforward way to change the sequence based specificities assigned to a detection assays (i.e. to change the nucleic acid domain that is conjugated to the analyte binding domain of a particular proximity probe that is used in a detection assay), e.g. so that a probe (or pair of probes) may be used in a different proximity detection format, or in conjunction with a different detection reagent, or in order to make different probe combinations. At present, the generation of a new proximity probe, i.e. an analyte binding domain and a different nucleic acid domain, requires the activation and conjugation of a new oligonucleotide molecule having a new sequence to an analyte binding domain.

As noted above, this increases the time and cost associated with generating new reagents for use in proximity-based detection assays.

SUMMARY OF THE INVENTION

The present invention seeks to overcome the above limitations in the manufacture of probes for use in proximity-based detection assays, and thus provides an improved method for the manufacture of proximity probes. More specifically, the present invention provides an improved method for the manufacture of a pair of proximity probes, which may be used in a proximity-based detection assay.

At its broadest, the present invention provides a method of manufacturing a pair of proximity probes, said pair comprising a first and a second proximity probe, wherein each proximity probe comprises an analyte binding domain and a partially double-stranded nucleic acid domain and each proximity probe of a pair can simultaneously bind to a target analyte, and wherein the nucleic acid domains of a pair of proximity probes are able to interact directly or indirectly upon binding of the pair of proximity probes to their target analyte, said method comprising:

a. conjugating a first universal oligonucleotide to a first analyte binding moiety to form a first universal conjugate;

b. conjugating a second, universal oligonucleotide to a second analyte binding moiety to form a second universal conjugate;

c. hybridising to the first universal oligonucleotide of the first universal conjugate a first tag oligonucleotide comprising a first universal complement domain which is complementary to the first universal oligonucleotide and a first unique domain which is not capable of hybridising to a first or second universal oligonucleotide, thereby to form a first proximity probe;

d. hybridising to the second universal oligonucleotide of the second universal conjugate a second, cognate, tag oligonucleotide comprising a second universal complement domain which is complementary to the second universal oligonucleotide and a second unique domain which is not capable of hybridising to a first or second universal oligonucleotide, thereby to form a second proximity probe;

wherein said first and second unique domains are capable of mediating an interaction, directly or indirectly, with each other, thereby enabling the nucleic acid domains of the first and second proximity probes to interact;

e. selecting a first and a second proximity probe, thereby to provide a pair of proximity probes.

The selecting step (e) is a step of matching a pair of probes together to make (or to provide) a proximity probe combination. Alternatively expressed, step (e) may be a step of pairing a first proximity probe with a cognate second proximity probe. As discussed further below cognate proximity probes comprise nucleic acid domains which are capable of interacting with each other. Step (e) may thus be seen as a step of combining a first and second proximity probe to make, or to obtain, a proximity probe pair. However, it will be understood in this respect that the combination can be made notionally, and does not necessarily require or involve physically combining the two members of the proximity probe (e.g. to make a physical mixture of first and second proximity probes). The first and second proximity probes may be combined (e.g. as a physical mixture) in use, when a proximity assay using the probes is preformed. In another embodiment, a combined pair of first and second proximity probes may be used together in a proximity assay without necessarily being provided, or used, in physical admixture. In other words they may both be used in the proximity assay, but may be provided or added to a test sample separately. Thus, in a combination or pair of proximity probes, the two probes need not be provided in admixture, but can be provided separately. Further a proximity probe pair can be provided as part of a larger set or panel (e.g. library) of proximity probes. For example a pair of proximity probes in a set or library may be designated for use together, e.g. as a pair of proximity probes according to the present invention.

By analogy, a pair of first and second tag oligonucleotides in a set or library of tag oligonucleotides may be designated for use together, or notionally paired, e.g. for use as part of a pair of proximity probes according to the present invention.

Thus, the present invention also provides a pair of proximity probes, said pair comprising a first and a second proximity probe, wherein each proximity probe comprises an analyte binding domain and a partially double-stranded nucleic acid domain and each proximity probe of a pair can simultaneously bind to a target analyte, and wherein the nucleic acid domains of a pair of proximity probes are able to interact directly or indirectly upon binding of the pair of proximity probes to their target analyte, wherein:

a. a first said proximity probe comprises a first universal oligonucleotide conjugated to a first analyte binding moiety and a first tag oligonucleotide hybridised to the first universal oligonucleotide, wherein the first tag oligonucleotide comprises a first universal complement domain which is complementary to the first universal oligonucleotide and a first unique domain which is not capable of hybridising to a first or second universal oligonucleotide; and b. a second said proximity probe comprises a second universal oligonucleotide conjugated to a second analyte binding moiety and a second, cognate, tag oligonucleotide hybridised to the second universal oligonucleotide, wherein the first tag oligonucleotide comprises a second universal complement domain which is complementary to the second universal oligonucleotide and a second unique domain which is not capable of hybridising to a first or second universal oligonucleotide, wherein said first and second unique domains are cognate domains capable of mediating an interaction, directly or indirectly, with each other, thereby enabling the nucleic acid domains of the first and second proximity probes to interact when said proximity probes have bound to their target analyte.

In the methods and kits of the invention the first and second universal oligonucleotides may be the same or different.

Such a pair of proximity probes may also be known as "hybridised probes", i.e. probes in which the tag oligonucleotide is hybridised to the universal conjugate.

A pair of proximity probes as described herein comprises a first and cognate second proximity probe having specificity for a particular target analyte, and comprising nucleic acid domains capable of interacting when said probes have bound to their target analyte. However, as noted above, it is not necessary that the first and second proximity probes are physically combined e.g. following their manufacture, and first and second proximity probes that are manufactured and/or selected or obtained separately are to be considered to comprise a pair of proximity probes. Each of a pair of proximity probes may therefore be selected and provided separately (e.g. as separate aliquots or in separate vessels), whilst still being considered as a constituent of a pair of proximity probes according to the present invention.

DETAILED DESCRIPTION

The problems associated with the manufacture of proximity probes outlined above are compounded when one considers that a number of proximity based detection assays have been adapted to be performed in multiplex, i.e. for the simultaneous or parallel detection of more than one target analyte in a sample (see for example the methods of WO2012/057689). The detection of multiple target analytes in a sample requires the generation of multiple different detectable signals, each of which can be detected separately within the sample. This is typically achieved through the use of multiple pairs of proximity probes, each pair of proximity probes having a different target analyte binding specificity, and comprising nucleic acid domains having at least one unique oligonucleotide sequence (i.e. that is not present in, or indicative of, a nucleic acid domain of another probe used in the detection assay).

Such methods typically require the manufacture of a plurality of pairs of proximity probes, and thus currently require the separate chemical activation of a plurality of different oligonucleotide molecules, and the separate conjugation of a plurality of different activated oligonucleotide molecules to a plurality of different target binding moieties. As noted above, the time and cost associated with generating proximity probes increase with the number of required probes. It will be apparent therefore that this represents a significant barrier to increasing the multiplexing aspect of proximity based detection assays.

The method of the present invention may therefore be employed in multiplex to provide an improved method for the generation of a plurality of pairs of proximity probes. Rather than conjugating a different oligonucleotide molecule to each of a plurality of first and each of a plurality of second analyte binding moieties (domains) (which would require the chemical activation of a plurality of different oligonucleotide domains), a single first universal oligonucleotide and a single second universal oligonucleotide may be conjugated to each of a plurality of first and second analyte binding domains, respectively. If the first and second universal oligonucleotides are the same, only a single species of universal oligonucleotide needs to be activated. This method thus reduces the number of activation and conjugation reactions that are required to manufacture a plurality of proximity probe pairs, as it merely requires the chemical activation of a single universal oligonucleotide (where the first and second universal oligonucleotides are the same) or two different first and second universal oligonucleotide molecules. This method thus overcomes many of the obstacles associated with the manufacture of multiple pairs of proximity probes, and provides an efficient, low cost, and high-quality manufacturing method for the manufacture of a plurality of pairs of proximity probes.

The present invention accordingly provides a method of manufacturing a plurality of pairs of proximity probes according to the method outlined above, wherein each pair of proximity probes comprises a first and a second proximity probe and wherein each pair is capable of binding to a different target analyte, said method comprising:

a. conjugating a first universal oligonucleotide to each of a plurality of first analyte binding moieties, to form a set of first universal conjugates;

b. conjugating a second universal oligonucleotide to each of a plurality of second analyte binding moieties, to form a set of second universal conjugates;

c. hybridising to the first universal oligonucleotide of the set of first universal conjugates one of a plurality of different first tag oligonucleotides, each different first tag oligonucleotide comprising a first universal complement domain which is common to all first tag oligonucleotides and which is complementary to the first universal oligonucleotide, and a first unique domain which is unique to each different first tag oligonucleotide and which is not capable of hybridising to a first or second universal oligonucleotide, thereby to form a plurality of first proximity probes;

d. hybridising to the second universal oligonucleotide of the set of second universal conjugates one of a plurality of different second cognate tag oligonucleotides, each different second tag oligonucleotide comprising a second universal complement domain which is common to all second tag oligonucleotides and which is complementary to the second universal oligonucleotide and a second unique domain which is unique to each different second tag oligonucleotide, and which is not capable of hybridising to a first or second universal oligonucleotide, thereby to form a plurality of second proximity probes;

e. selecting multiple first proximity probes from said plurality of first proximity probes and multiple cognate second proximity probes from said plurality of second proximity probes, thereby to provide a plurality of pairs of proximity probes.

The present invention thus provides a method for the production of a plurality of pairs of proximity probes in which only one or two universal oligonucleotides need be chemically activated and separately conjugated to each of a plurality of different target analyte binding moieties, each having a different target analyte binding specificity simultaneously and in parallel. Thus rather than conjugating a plurality of different oligonucleotides (nucleic acid domains to a pair of analyte binding domains, only one or two universal oligonucleotides are conjugated, to form a pair (first and second) universal conjugates. These universal conjugates may then be used to prepare a plurality of different proximity probes having different nucleic acid domains, by hybridising different tag oligonucleotides to the universal conjugates. As fewer separate activation reactions are required (i.e. only 1 or 2), this may take place in large batches, thus allowing a far greater degree of consistency to be achieved for the conjugation of oligonucleotide molecules to the proximity probes. Both batch-to-batch consistency and consistency within a plurality of oligonucleotides may thus be improved, as each analyte binding domain will be coupled to its universal oligonucleotide to substantially the same degree. Hybridisation of tag oligonucleotides to the universal oligonucleotides may also be performed using a far lower amount of oligonucleotide than would be required to conjugate an equivalent oligonucleotide to the analyte binding domain, and thus synthesis of each of the tag oligonucleotides may be performed on a smaller scale than is possible using current methods. This further reduces the costs associated with proximity probe production.

The terms "analyte binding moiety" and "analyte binding domain" have the same meaning and are used interchangeably herein. However, in one embodiment the analyte binding moiety may be viewed as the moiety to which the universal oligonucleotides are attached (conjugated) to form the analyte binding domain of the proximity probe. An analyte binding domain may thus be viewed as the analyte binding moiety which is attached to the universal oligonucleotide or to the nucleic acid domain of a proximity probe.

Furthermore, the present invention allows the straightforward 'switching' of the nucleic acid domain that is associated with a particular target analyte detection assay employed in a detection assay. As the tag oligonucleotides, which comprise a unique domain, are only bound to the analyte binding domain by hybridisation via a region of complementarity to the universal oligonucleotides rather than by covalent conjugation, it would be considered trivial to provide conditions which would disrupt the hybridisation between a tag oligonucleotide and a universal oligonucleotide (e.g. by heating), thereby to allow the tag oligonucleotide to dissociate from the analyte binding domain. A further, different tag oligonucleotide may subsequently be allowed to hybridise to the universal domain instead. This may be done e.g. to change the sequence specificity assigned to a particular assay (e.g. if the sequence is found to be difficult to detect or interacts with a different, non-cognate sequence present in the sample), or in order to change the assay that may be performed to detect the particular analyte, e.g. from a proximity extension assay to a proximity ligation assay. Assays which may be performed using the probes manufactured by the methods of the present invention are discussed in more detail below, and the skilled person would understand how the unique domain of a tag oligonucleotide might be designed in order to be suitable for use in a given assay.

The universal oligonucleotides may be seen as universal adapters (i.e. first and second universal adaptors) to allow the hybridisation of a tag oligonucleotide (e.g. one of a plurality of tag oligonucleotides) comprising a unique and specific sequence, to the first or second universal conjugates. Each of a plurality of first and second tag oligonucleotides, each comprising a unique domain and a universal domain may thereby hybridise to each of a set of the first or second universal oligonucleotides conjugated to the first or second analyte binding domains, resulting in a plurality of pairs of probes, each pair having a different target analyte binding specificity, and comprising nucleic acid domains which are capable of interacting directly or indirectly upon binding of the pair of proximity probes to their respective target analyte. The universal complement domain (and by corollary the universal oligonucleotide) may be viewed as a universal hybridisation site.

In a further aspect, the present invention provides a plurality of pairs of proximity probes as defined above, wherein each pair of proximity probes comprises a first and a second proximity probe and wherein each pair is capable of binding to a different target analyte, wherein:

a. each of the plurality of first proximity probes comprise a first universal oligonucleotide conjugated to a first analyte binding moiety and one of a plurality of different first tag oligonucleotides hybridised to the first universal oligonucleotide, wherein each different first tag oligonucleotide comprises a first universal complement domain which is common to all first tag oligonucleotides and which is complementary to the first universal oligonucleotide, and a first unique domain which is unique to each different first tag oligonucleotide and which is not capable of hybridising to a first or second universal oligonucleotide; and b. each of the plurality of second proximity probes comprise a second universal oligonucleotide conjugated to a second analyte binding moiety and one of a plurality of different second cognate tag oligonucleotides hybridised to the second universal oligonucleotide, wherein each different second tag oligonucleotide comprises a second universal complement domain which is common to all second tag oligonucleotides and which is complementary to the second universal oligonucleotide, and a second unique domain which is unique to each different second tag oligonucleotide and which is not capable of hybridising to a first or second universal oligonucleotide;

wherein said first and second unique domains of each pair of proximity probes are cognate domains capable of mediating an interaction, directly or indirectly, with each other, thereby enabling the nucleic acid domains of the first and second proximity probes to interact when said proximity probes have bound to their target analyte.

A pair of proximity probes is capable of binding simultaneously to the target analyte, thereby bringing their nucleic acid domains into proximity. The first and second proximity probes of a pair of proximity probes may therefore be seen as being paired, or as being cognate to one-another. Alternatively expressed, the first and second members of a proximity probe pair may be described as "matched". A first proximity probe may thus be mentioned with reference to its cognate or matched proximity probe, i.e. the second proximity probe of a pair which has an analyte binding domain capable of binding to the same target analyte in a sample. Notably, these do not need to be physically combined in order to be considered a 'pair' of proximity probes, and thus a first and a separate cognate second proximity probe represent a pair of proximity probes. The term "cognate" or "matched" as used herein thus means simply that the proximity probes form, or are part of, a functional pair to be used together in a proximity assay. More particularly "cognate" or "matched" nucleic acid domains, tag oligonucleotides or unique domains are capable of interacting, directly or indirectly, with one another, i.e. are a pair of interacting domains or oligonucleotides. In other words, they may interact with one another, directly or indirectly, to generate, or to lead to the generation of, a signal, more particularly a signal by means of which the target analyte (the analyte which is the target of the proximity assay) may be detected.

First and second (or each of a plurality of first and second) proximity probes are selected (or obtained) according to the methods described herein, thereby to obtain a cognate pair (or plurality of cognate pairs) of proximity probes. A matched pair of proximity according to the present invention does not, however, need to be physically combined (e.g. by admixing) in order to be considered a cognate pair of proximity probes; first and second proximity probes according to the present invention (i.e. comprising first and second universal domains and nucleotide domains conjugated thereto) may thus be selected and provided separately (e.g. as separate aliquots in separate vessels). A pair of proximity probes may, for instance, be selected separately and only be combined in use by a person wishing to detect a particular target analyte in a sample. Nevertheless, a first and second proximity probe should be considered to be a pair of proximity probes regardless of whether or not they are physically combined.

Each of a plurality of first or second proximity probes may similarly be selected or provided separately, and still represent a plurality of first proximity probes or a plurality of second proximity probes, respectively.

The analyte binding domain of the proximity probe may be any molecule capable of selectively binding to a target molecule. For example, the binding domain may be selected from a protein, such as an antibody, which term is used broadly herein to include any type of antibody or antibody-derived molecule and thus includes a monoclonal or polyclonal antibody, chimeric antibody, antibody fragment (e.g. Fab or Fv) or derivative thereof (e.g. scFv or diabody), lectin, soluble cell surface receptor, combinatorially derived protein from phage display or ribosome display, peptide, carbohydrate, nucleic acid, such as an aptamer or a nucleic acid molecule comprising the complementary sequence for a target nucleic acid, or combinations thereof. In a preferred embodiment of the invention, the analyte binding domain is a protein, preferably an antibody or derivative or fragment thereof.

In a particular aspect of the present invention, among a plurality of pairs of proximity probes of the invention comprising pairs of proximity probes capable of binding to two or more different target analytes in a sample, each pair of proximity probes in a plurality of proximity probe pairs will preferably have a binding specificity towards a different target analyte. In other words, each first proximity probe and its cognate second proximity probe will be capable of binding to a different target analyte, and only one first proximity probe and its cognate second proximity probe among a plurality of proximity probe pairs will be capable of binding a particular target analyte.

The nucleic acid domain of the proximity probes described herein (i.e. comprising a universal oligonucleotide and a tag oligonucleotide) is conjugated to the analyte binding domain of the proximity probe via the universal oligonucleotide. The universal oligonucleotide may be conjugated to the analyte binding domain by its 5' or 3' end, and thus the 3' or 5' end of the universal oligonucleotide may be free to hybridise to its complementary sequence in a tag oligonucleotide as appropriate (i.e. the tag oligonucleotide may comprise a free 3' or 5' end as appropriate).

A tag oligonucleotide comprises a universal complement domain which is complementary to the universal oligonucleotide, and can thereby hybridise to the universal oligonucleotide in an antiparallel manner via Watson-Crick or analogous base pairing. In one aspect of the present invention, the first and second universal oligonucleotides may be different, i.e. a first universal oligonucleotide may be conjugated to a first analyte binding moiety, and a second, different, oligonucleotide may be conjugated to a second analyte binding moiety. Thus, the first and second universal conjugates may comprise different universal oligonucleotides following conjugation of the first and second universal oligonucleotides to the respective analyte binding moieties. In such an aspect, the universal complement domains of the first and second tag oligonucleotides will also be different, and will be complementary to the first and second universal oligonucleotides, respectively.

However, in another aspect of the present invention, the first and second universal oligonucleotides may be the same i.e. the same universal oligonucleotide may be conjugated to the first and second analyte binding domains. In other words, the first and second universal conjugates may comprise the same universal oligonucleotides following the conjugation of the universal oligonucleotides to the analyte binding moieties. Accordingly, in such an aspect, the universal complement domains of the first and second tag oligonucleotides will also be the same, and will be complementary to the same universal oligonucleotide sequence.

The tag oligonucleotides further comprise unique domains which are not capable of hybridising to a universal oligonucleotide. The universal complement domain may therefore be situated towards the 5' end or towards the 3' end of the tag oligonucleotide, depending on how the tag oligonucleotide is required to function in a detection assay (i.e. whether the unique domain is required to be situated at the 3' or 5' end of the tag oligonucleotide). The nucleic acid domain of a proximity probe is thus partially double-stranded, i.e. it comprises a double-stranded region (comprising the universal oligonucleotide hybridised to the universal complement domain of tag oligonucleotide) and a single-stranded region (comprising the unique domain of the tag oligonucleotide with a free 3' or 5' end). In other words, the proximity probes may be seen to comprise a free single-stranded end (the unique domain of the tag oligonucleotide), which is available for interaction with another oligonucleotide molecule present in a sample (e.g. the nucleic acid domain of another proximity probe, or a common hybridisation template etc.), as discussed in more detail below.

As will be described in more detail below, the unique domains may comprise more than one domain or "functional region". Thus a unique domain may comprise multiple different domains or regions (e.g. 2, 3, 4 or more different domains). This may depend on the nature of the proximity assay in which the probe is to be used, how proximity probe interaction is to be detected, whether the product of proximity probe interaction is to be amplified, whether the assay is performed in multiplex etc. For example, the unique domain may contain one or more common or universal domains/regions (common or universal sequences), e.g. primer binding sites for universal primers or sequences for immobilisation etc, and one or more unique regions or unique sequences (e.g. tag sequences). By way of representative example, a unique domain may contain one common or universal sequence and two unique sequences.

In a further embodiment, a tag oligonucleotide may contain one or more additional domains, which may be unique domains and/or universal or common domains.

As noted above, the nucleic acid domains of a pair of proximity probes are designed to interact and accordingly the first and second tag oligonucleotides of a pair of proximity probes may also be viewed as 'cognate' or 'matched' (or paired) to each other. That is to say, a cognate or matched pair of proximity probes that are both capable of binding to a common target analyte comprises first and second tag oligonucleotides which are capable of interacting, either directly or indirectly when in proximity to one-another, upon binding of the pair of proximity probes to their target analyte.

The second tag oligonucleotide of the second proximity probe may thus be seen as 'cognate' or 'matched to' to, or 'paired with' the first tag oligonucleotide of the first proximity probe within a pair, and a tag oligonucleotide will only interact with its corresponding cognate partner and will not interact (either directly or indirectly) with a tag oligonucleotide from another proximity probe, i.e. an oligonucleotide which is not its cognate partner. Although the nucleic acids may be described as 'cognate', this does not necessarily mean that the respective oligonucleotides are homologous or related to each other in any way, or share any features (e.g. structural or sequence features); rather, the term 'cognate' means that a tag oligonucleotide is capable of interacting with the tag oligonucleotide of the other proximity probe in a proximity probe pair. However, in some embodiments, as will be described in more detail below, the nucleic acid domains, or more particularly the unique domains thereof may be complementary to each other such that they may hybridise to each other.

In a particular aspect of the present invention, the tag oligonucleotide of a first proximity probe will only be capable of interacting with the tag oligonucleotide of its cognate partner, i.e. the second proximity probe which binds to the same target analyte. A tag oligonucleotide may therefore, in one embodiment, not be capable of interacting with a further nucleic acid domain of a proximity probe present in a sample.

Among a plurality of proximity probes, it may be desirable that the tag oligonucleotide of a proximity probe will not interact (either directly or indirectly) with a tag oligonucleotide from a non-cognate proximity probe, i.e. a tag oligonucleotide from a proximity probe which is capable of binding to a different target analyte. Thus, a first tag oligonucleotide may preferably only be capable of binding to the second tag oligonucleotide of its cognate proximity probe, or the tag oligonucleotides of a cognate pair of probes may only be capable of binding to a complementary nucleic acid molecule or oligonucleotide (e.g. a hybridisation template) which is specific for (e.g. particular to or dedicated to) that probe pair, and not to a complementary nucleic acid molecule or oligonucleotide provided for a different proximity probe pair. Put another way, a first tag oligonucleotide may only interact with its cognate second tag oligonucleotide. Thus, in one embodiment, among a plurality of pairs of proximity probes, each first tag oligonucleotide is only able to interact with a single second tag oligonucleotide.

However, among a plurality of pairs of proximity probes, it may, in certain embodiments, be desirable for a particular first tag oligonucleotide to be capable of interacting with more than one second tag oligonucleotide or vice versa, or indeed for a plurality of first tag oligonucleotides to be able to interact with a plurality of second tag oligonucleotides. Thus, alternatively, a plurality of first tag oligonucleotides may be capable of interacting with the same second tag oligonucleotide. Similarly, each of a plurality of first tag oligonucleotides may be capable of interacting with a plurality of second tag oligonucleotides. In other words, among a plurality of pairs of proximity probes, at least one first tag oligonucleotide may be able to interact with more than one second tag oligonucleotide. This may be useful for example in a situation where the target analyte is an interaction or a complex (e.g. between 2 proteins or 2 subunits of a protein) and different interactions/complexes are possible and it is desired to detect or determine which of a number of different proteins or subunits have interacted or complexed. A plurality of proximity probes may be used, each capable of binding to one possible member of a complex or interaction, and said probe may be paired with (or cognate to) to a number (plurality) of second proximity probes capable of binding to different or alternative possible members of an interaction or complex. There may also be other circumstances where it may be desirable for a proximity probe to be paired with or cognate to a plurality of other (e.g. second) proximity probes. It may in such a situation be desirable to distinguish which probe (e.g. specific for which analyte/analyte binding site/member of a complex or interaction) has paired with which other, or second, probe (in other words, which probes have bound to the target analyte in proximity). Thus in such a situation the unique domain of the tag oligonucleotide may comprise a common sequence, or common domain, as well as a unique sequence. In other words, the unique domain may not be unique in its entirety.

Accordingly a unique domain of a tag oligonucleotide may comprise a common sequence and a unique sequence. In a particular embodiment, the common sequence (or common domain) may mediate the interaction between first and second tag oligonucleotides (and hence of the nucleic acid domains) and the unique sequence may be used to distinguish or identify (i.e. to tag) the proximity probe. The unique sequence may thus be viewed as a tag sequence (or domain) or as an identification sequence (or domain).

Thus, in a particular embodiment of the present invention, among a plurality of pairs of proximity probes, each first tag oligonucleotide may comprise a common sequence in its unique domain, and each second tag oligonucleotide may comprise a common sequence in its unique domain, which common sequences (preferably situated at the free ends of the respective unique domains) are capable of mediating the interaction between the tag oligonucleotides.

The tag oligonucleotides of the present invention may be viewed in the same way as the nucleic acid domains of proximity probes known in the art, i.e. probes manufactured by conventional means, by the conjugation of functional nucleic acid molecules directly to analyte binding domains. The tag oligonucleotides may therefore interact by their free ends in the same manner as nucleic acid domains of proximity probes already known in the art.

The interaction between the free ends of the nucleic acid domains of a pair of proximity probes (i.e. the free ends of the tag oligonucleotides) may be direct or indirect. For example, in some embodiments, the free ends of the tag oligonucleotides may comprise a region of complementarity to one another, i.e. they are able to hybridise to one-another in an antiparallel manner by Watson-Crick or other base pairing, thereby to form a region of duplex. Alternatively, the nucleic acid domains may interact indirectly, i.e. their interaction may be mediated by a further nucleic acid molecule (e.g. oligonucleotide) that is added to a sample, and which is able to hybridise to one or more of the nucleic acid domains. The further, or added, nucleic acid molecule may accordingly in one embodiment be viewed as a common template, more particularly common hybridisation template, for the nucleic acid domains (e.g. a common molecule to which both the nucleic acid domains, or more particularly the tag oligonucleotides/unique domains thereof may hybridise. The common template may act to template a ligation reaction, e.g. the ligation of the nucleic acid domains (tag oligonucleotides) to each other. Alternatively, the nucleic acid domains may together act as ligation templates for the ligation of one or more added oligonucleotides, in particular an intra- or inter-molecular ligation to form a circular nucleic acid molecule which can be detected by amplification with an RCA reaction. In a further embodiment, one or more nucleic acid domains (tag oligonucleotides) may template ligation and one nucleic acid domain may contribute to or mediate interaction in another (or additional) way, e.g. by acting as primer for RCA. The means by which the interaction between the tag oligonucleotides is mediated may therefore be chosen based on the detection method for which the proximity probes of the present invention are required, as discussed in more detail below.

In one embodiment, the unique domain of at least one tag oligonucleotide has a free 3' end, which is able to hybridise directly or indirectly (i.e. mediated by a further oligonucleotide molecule) to a region of complementarity within the unique domain of the tag oligonucleotide of the other proximity probe in a pair when the probes bind to a target analyte in proximity, thereby forming a duplex. Said free 3' ends may hybridise directly to each other via a region of complementarity.

Other hybridisation formats are also possible, for example wherein the tag oligonucleotide of one proximity probe has a free 3' end and the other a free 5' end, wherein the tag oligonucleotides (or more particularly portions of the tag oligonucleotides) may hybridise to one another or to a common hybridisation template, or two tag oligonucleotides with free 3' ends (or more particularly portions thereof) hybridise to a common hybridisation template (e.g. an added oligonucleotide molecule), in each case there being at least one 3' end available following hybridisation. Various examples of how probes may interact are shown in WO 2012/104261, which is hereby incorporated by reference in its entirety.

In preferred embodiments, following hybridisation, one or more of the hybridised molecules (e.g. tag oligonucleotides/unique domains) may be extended by a polymerase-catalysed chain extension reaction and the extension product may be detected. Such an interaction forms the basis of a so-called proximity extension assay (PEA). Thus, the proximity probes of, or manufactured according to, the present invention are preferably for use in a PEA. PEAs are described in more detail in WO2012104261, WO0161037 and WO2013113699.

As noted above, the probes of the present invention may also be used in proximity-dependent assays based on ligation (i.e. a proximity ligation assay, or PLA) (i.e. wherein at least first and second proximity probes comprise nucleic acid domains and the interaction between them involves a ligation reaction). Viewed generally, the nucleic acid domains of the probes may mediate (e.g. take part in, directly or indirectly), a ligation reaction. Such a ligation reaction may involve ligation of the nucleic acid domains of the proximity probes, and/or the nucleic acid domain(s) may template a ligation reaction.

In one format, the nucleic acid domains may bind to one or more splint oligonucleotides (a common template), which mediates their interaction (specifically in the case of ligation, the splint oligonucleotide which hybridises to the domains may act as a template for the ligation reaction) and the splint assists in or mediates this interaction. In other formats/embodiments, the splint may be provided as the nucleic acid domain of a third proximity probe. The nucleic acid domains may be ligated to each other directly or indirectly. In the case of a direct ligation, the ends of the domains hybridise to the splint adjacent to one another, such that they may be ligated to each other directly. In the case of an indirect ligation the ends of domains hybridise to the splint with a gap therebetween, which gap may be filled by hybridisation of a further gap oligonucleotide, to which the ends of the nucleic acid domains are respectively ligated, or the gap may be filled by extending a hybridised 3' end of a nucleic acid domain, prior to ligation. Thus, a PLA may include an extension reaction and may also be viewed a PEA, at least in part. Various PLA embodiments, including such "gap-fill" embodiments, are well-described in the literature, for example in WO 01/61037 or in WO 2007/107743, WO9949079, WO03012119.

In a further specific example, one of more of the nucleic acid domains of the proximity probes, (specifically the unique domain (or free end) of the nucleic acid domain), may act to template the ligation of one or more added oligonucleotides. In one such embodiment, a first added oligonucleotide may hybridise to both nucleic acid domains, and one or more further oligonucleotides may be added which hybridise to only one of the domains, for example one to each of the nucleic acid domains, each adjacent to each end of the first oligonucleotide, which may be ligated to the first oligonucleotide in a reaction templated by the nucleic acid domains.

In alternative embodiments, an added oligonucleotide(s) may be circularised by the ligation reaction. Thus, by way of example the nucleic acid domains of a pair of proximity probes, which are attached to the analyte binding domains of the respective probes via universal oligonucleotides, may have complementarity, respectively, to (i) the 5' and 3' ends, and (ii) region between said ends, of an added linear oligonucleotide (akin to a "padlock probe"). By binding to said added oligonucleotide(s) the probes may be said to be interacting indirectly. When both probes of the proximity probe pair are brought into proximity due to binding to the same analyte, the nucleic acid domains of the respective probes are able to hybridise to the respective parts of the added oligonucleotide. The nucleic acid domain with complementarity to the 5' and 3' ends of the added oligonucleotide templates the juxtaposed hybridisation, and ligation (on addition of an appropriate ligase enzyme), of said ends, resulting in circularisation of the added oligonucleotide. This circularised oligonucleotide is then detected by rolling circle amplification (RCA) using the other nucleic acid domain as a primer; the nucleic acid domain of the other probe of the pair, which is hybridised to a region of the added oligonucleotide between the ligated ends, has a free 3' end.

It will be appreciated that the single added oligonucleotide can be replaced by two oligonucleotides which may be ligated together to form a circle (such a ligation may be templated by one or both nucleic acid domains, but one of the domains will have a free 3' end to act as a primer).

In particular embodiments of the present invention, the unique domain of at least one of the tag oligonucleotides of a pair of proximity probes may comprise one or more regions of secondary structure, e.g. a stem-loop structure or a hairpin. Said region of secondary structure may be unfolded in order to allow the interaction between a cognate pair of tag oligonucleotides by any convenient means, e.g. enzymatic cleavage. Methods of unfolding probes comprising a region of secondary structure are discussed in greater detail in WO2012/152942, the content of which is hereby incorporated by reference in its entirety. In a particularly preferred aspect, upon the proximity binding of a pair of proximity probes, the unique domain of a first tag oligonucleotide may interact with any such region of secondary structure, e.g. by invasion of a stem loop structure, thereby to unfold it. The region of secondary structure may thus be viewed as a metastable secondary structure, i.e. a secondary structure which is thermodynamically unstable, but kinetically stable.

The term "hybridisation" or "hybridises" as used herein refers to the formation of a duplex between nucleotide sequences which are sufficiently complementary to form duplexes via Watson-Crick, or other, base pairing. Two nucleotide sequences are "complementary" to one another when those molecules share base pair organization homology. Hence, a region of complementarity in a tag oligonucleotide refers to the portion of the tag oligonucleotide (the universal complement domain) that is capable of forming an intermolecular duplex with its respective universal oligonucleotide (i.e. a first or second universal oligonucleotide). Similarly, the unique domains of a pair of tag oligonucleotides may interact directly or indirectly upon binding of the pair of proximity probes to their target analyte; said interaction may thus result in the formation of an intermolecular duplex, either between the free ends of the two tag oligonucleotides, or between each of the free ends of the two tag oligonucleotides and a third oligonucleotide molecule (e.g. a splint oligonucleotide or common nucleic acid molecule).

"Complementary" nucleotide sequences will combine with specificity to form a stable duplex under appropriate hybridization conditions. For instance, two sequences are complementary when a section of a first sequence can bind to a section of a second sequence in an anti-parallel sense wherein the 3'-end of each sequence binds to the 5'-end of the other sequence and each A, T(U), G and C of one sequence is then aligned with a T(U), A, C and G, respectively, of the other sequence. RNA sequences can also include complementary G=U or U=G base pairs. Thus, two sequences need not have perfect homology to be "complementary" under the invention. Usually two sequences are sufficiently complementary when at least about 85% (preferably at least about 90%, and most preferably at least about 95%) of the nucleotides share base pair organization over a defined length of the molecule.

Detection of an analyte in a proximity-based detection assay depends upon the presence of an analyte in a sample and detecting the interaction between a pair of proximity probes, when such probes are bound to the analyte. The interaction between the probes (or more specifically, between their respective cognate nucleic acid domains) is thus proximity-dependent; the binding of the proximity probes, together, on the analyte brings them into proximity, such that they (or more particularly, their nucleic acid domains) may interact.

At least one of the first and second tag oligonucleotides of a proximity probe pair will preferably comprise in its unique domain a sequence that is specific to, and representative of, the particular target analyte which is the target for that particular pair of proximity probes (a unique tag sequence). This may be a "unique sequence" as discussed above. The interaction of the nucleic acid domains of a pair of proximity probes may give rise to a nucleic acid sequence which was not previous present in the sample, and that may comprise the unique tag sequence discussed above, i.e. a detectable signal that can be detected specifically (e.g. that can be distinguished from the detectable signal from a different proximity probe pair). Thus, in general terms the interaction between the nucleic acid domains of a pair of proximity probes (i.e. between the free ends of first and second tag oligonucleotides) leads to the generation of a nucleic acid product (a detectable signal), which may be detected in order to detect the analyte. Thus the analyte may be detected by detecting said detectable signal.

Conversely, among a plurality of pairs of proximity probes, each proximity probe pair may comprise in a unique domain thereof a sequence that is common to (i.e. shared by) each of the proximity probe pairs (a universal tag sequence). Said sequence may be used e.g. as a primer binding site to allow the amplification of the nucleic acid molecule formed as a result of the interaction between the proximity probes, or may be used to immobilise or otherwise handle or manipulate the nucleic acid molecule generated.

Detection of the detectable signal generated on the interaction of the tag oligonucleotides may be performed directly or indirectly. The direct detection of a signal may be achieved using e.g. a detection oligonucleotide comprising a label that may be selected from, but is not limited to, any one or more of fluorophores, fluorescent proteins, radioactive isotopes, colorimetric detection labels such as chromogens, magnetic particles, particles such as carbon, silver or gold, quantum dots, enzymes. Thus, the label of the marker may be directly "signal-giving".

Alternatively, the detection may be indirect, by which is meant the detectable signal must be manipulated or enhanced to make it detectable. For example, the detectable signal may require some further treatment, e.g. it may be amplified, e.g. by any suitable method known in the art. Thus a nucleic acid molecule formed or generated as a result of the interaction, e.g. a ligation and/or extension product, may be amplified. Amplification may be linear or exponential, as desired, where representative amplification protocols of interest include, but are not limited to: polymerase chain reaction (PCR); isothermal amplification, rolling-circle amplification (RCA), and their well-known variants, such as hyperbranched RCA, etc. Other nucleic acid amplification methods may include Loop mediated isothermal amplification (LAMP), SMart Amplification Process (SMAP), Nucleic acid sequence based amplification (NASBA), or ligase chain reaction (LCR). Where the detection step includes an amplification, the amplification product may be detected, thereby to detect a target analyte.

An amplification product may be detected non-specifically or specifically, as described in greater detail below. Representative non-specific detection protocols of interest include protocols that employ signal producing systems that selectively detect double stranded DNA products, e.g., via intercalation. Representative detectable molecules that find use in such embodiments include fluorescent nucleic acid stains, such as phenanthridinium dyes, including monomers or homo- or heterodimers thereof that give an enhanced fluorescence when complexed with nucleic acids. Examples of phenanthridinium dyes include ethidium homodimer, ethidium bromide, propidium iodide, and other alkylsubstituted phenanthridinium dyes. In another embodiment of the invention, the nucleic acid stain is or incorporates an acridine dye, or a homo- or heterodimer thereof, such as acridine orange, acridine homodimer, ethidium-acridine heterodimer, or 9-amino-6-chloro-2-methoxyacridine. In yet another embodiment of the invention, the nucleic acid stain is an indole or imidazole dye, such as Hoechst 33258, Hoechst 33342, Hoechst 34580 (BIOPROBES 34, Molecular Probes, Inc. Eugene, Oreg., (May 2000)) DAPI (4',6-diamidino-2-phenylindole) or DIPI (4',6-(diimidazolin-2-yl)-2-phenylindole). Other permitted nucleic acid stains include, but are not limited to, 7-aminoactinomycin D, hydroxystilbamidine, LDS 751, selected psoralens (furocoumarins), styryl dyes, metal complexes such as ruthenium complexes, and transition metal complexes (incorporating Tb3+ and Eu3+, for example). In certain embodiments of the invention, the nucleic acid stain is a cyanine dye or a homo- or heterodimer of a cyanine dye that gives an enhanced fluorescence when associated with nucleic acids. Any of the dyes described in U.S. Pat. No. 4,883,867 to Lee (1989), U.S. Pat. No. 5,582,977 to Yue et al. (1996), U.S. Pat. No. 5,321,130 to Yue et al. (1994), and U.S. Pat. No. 5,410,030 to Yue et al. (1995) (all four patents incorporated by reference) may be used, including nucleic acid stains commercially available under the trademarks TOTO, BOBO, POPO, YOYO, TO-PRO, BO-PRO, PO-PRO and YO-PRO from Molecular Probes, Inc., Eugene, Oreg. Any of the dyes described in U.S. Pat. No. 5,436,134 to Haugland et al.(1995), U.S. Pat. No. 5,658,751 to Yue et al. (1997), and U.S. Pat. No. 5,863,753 to Haugland et al. (1999) (all three patents incorporated by reference) may be used, including nucleic acid stains commercially available under the trademarks SYBR Green, EvaGreen, SYTO, SYTOX, PICOGREEN, OLIGREEN, and RIBOGREEN from Molecular Probes, Inc., Eugene, Oreg. In yet other embodiments of the invention, the nucleic acid stain is a monomeric, homodimeric or heterodimeric cyanine dye that incorporates an aza- or polyazabenzazolium heterocycle, such as an azabenzoxazole, azabenzimidazole, or azabenzothiazole, that gives an enhanced fluorescence when associated with nucleic acids, including nucleic acid stains commercially available under the trademarks SYTO, SYTOX, JOJO, JO-PRO, LOLO, LO-PRO from Molecular Probes, Inc., Eugene, Oreg.

A universal oligonucleotide may be of any length sufficient to allow the hybridisation of a tag oligonucleotide via its universal complement domain. Thus, the universal oligonucleotide may be 5-40 nt in length, preferably 15-30 nt in length. In a particular embodiment, the universal oligonucleotide may be around 20 nt in length, e.g. 15, 16, 17, 18, 19, 20, 21, 22, 23, 24 or 25 nt in length. However, the first and second universal oligonucleotides, which in certain embodiments of the present invention may have different sequences, may be of different lengths, or may be the same length. The universal complement domains of the tag oligonucleotides may preferably be the same length as the universal oligonucleotides, however, the universal complement domain need not hybridise to the entire universal oligonucleotide, and may in certain embodiments hybridise only to a portion thereof.

The interaction between a universal oligonucleotide and the universal complement domain of the tag oligonucleotide should be stable, i.e. such that the duplex formed does not dissociate under the conditions of the detection reaction. In a preferred embodiment, the melting temperature (Tm) of the duplex formed is greater than 45° C. For example, the Tm may be at least 50° C., greater than 55° C., greater than 60° C. or greater than 65° C. Preferably, where the first and second universal oligonucleotides are different, the respective Tm values of the duplexes formed between the first and second tag oligonucleotides and the first and second universal oligonucleotides will be similar (i.e. within 10° C., preferably within 5° C. or less) or the same. Methods and formulae for calculating Tm values for a given nucleotide sequence are known in the art. Approximate Tm values may be calculated for example by using the formula: $Tm=4° C.\times(G+C)+2° C.\times(A+T/U)$. Software for the calculation of Tm values is also known in the art.

In a further preferred embodiment of the present invention, where a plurality of pairs of proximity probes are used in a multiplexed detection format, one or both of the tag oligonucleotides may comprise a universal tag sequence, which may be used in further analysis or detection steps. In one embodiment this may comprise a universal primer binding site, i.e. so that a common single forward and/or reverse amplification primer may be used in the amplification of a plurality of nucleic acid molecules generated through the interaction of a plurality of proximity probe pairs in any of the detection methods outlined herein. In another embodiment, the universal tag sequence may comprise a binding site for separation of the proximity probe and/or the detectable signal. The universal tag sequence may for example be immobilisable, e.g. it may be capable of hybridising to a capture oligonucleotide provided on a solid surface or support, or it may be provided with means for attachment to a solid surface or support, such as a member of an affinity binding pair for example, the other member or which is provided on the support/surface.

The terms "plurality" means more than one, i.e. at least 2. Thus, a plurality of pairs of proximity probes refers to at least 2 pairs of proximity probes, each capable of binding to a different target analyte. Preferably this refers to at least 3, 4, 5, 6, 7, 8, or 9 pairs of proximity probes, or more, e.g. at least 10, 20, 50, 100, 200, 500, 1000 or more pairs of proximity probes. Similarly, the term "multiplex" or "multiplexed" refers to performing a method (e.g. the detection of an analyte or the manufacture of a pair of probes) simultaneously and in parallel for more than one item at a time, as defined above. Thus, by way of representative example, a plurality of pairs of proximity probes may be used for the multiplex detection of a plurality of different target analytes.

As discussed above, in order for a target analyte to be detected in a proximity based detection assay, a pair of proximity probes bind to a common target, thereby bringing their respective nucleic acid domains (or more particularly in the present case the free ends, or unique domains, of the tag oligonucleotides) into proximity with each other, and allowing them to interact. The nature of the target analyte is therefore not limiting on the present invention, provided that suitable analyte binding domains, having specificity for the target analyte, may be found.

The "analyte" may be any substance (e.g. molecule) or entity it is desired to detect in a detection assay. The analyte may be viewed as the "target" of an assay method. The analyte may accordingly be any biomolecule or chemical compound it may be desired to detect, for example a peptide or protein, or nucleic acid molecule or a small molecule, including organic and inorganic molecules. The analyte may be a cell or a microorganism, including a virus, or a fragment or product thereof. It will be seen therefore that the analyte can be any substance or entity for which a specific binding partner (e.g. an affinity binding partner) can be developed. All that is required is that the analyte is capable of binding a pair of proximity probes.

Proximity probe-based assays have found particular utility in the detection of proteins or polypeptides. Analytes of particular interest may thus include proteinaceous molecules such as peptides, polypeptides, proteins or prions or any molecule which includes a protein or polypeptide component, etc., or fragments thereof.

A first and second proximity probe may both comprise the same analyte binding domains, or the analyte binding domain of each of the proximity probes in a pair may be different, depending on the target analyte that is to be detected.

In one embodiment, a pair of proximity probes of the present invention may be used to detect a target analyte that comprises a single molecule i.e. the first and second proximity probes comprise different analyte binding domains and may bind simultaneously to two different regions (or epitopes) of the target analyte, i.e. a single target analyte may be bound simultaneously by two different (cognate) proximity probes. The target analyte may thus be considered polyepitopic, i.e. comprising multiple epitopes, each of which may be targeted by a different proximity probe. Thus, in this embodiment, the pair of proximity probes (comprising first and second proximity probes) comprises first and second analyte binding domains that are different, and that have different binding specificities. The present invention thus provides a method of detecting a target analyte using the probes of the present invention, wherein the target analyte is a single molecule, wherein the analyte binding domains of the first and second proximity probes are different, and wherein the first and second proximity probes bind to different epitopes within the target analyte.

In a further embodiment, a pair of probes of the present invention may be used to detect a complex of two or more molecular subunits, which may or may not be covalently bound to one another, and which may be the same or different. Thus in addition to cells or microorganisms, such a complex analyte may also be a protein complex or protein interaction. Such a complex or interaction may thus be a homo- or hetero-multimer. Aggregates of molecules, e.g. proteins may also be target analytes, for example aggregates of the same protein or different proteins. The analyte may also be a complex between proteins or peptides and nucleic acid molecules such as DNA or RNA. Of particular interest may be the interactions between proteins and nucleic acids, e.g. between regulatory factors, such as transcription factors, and DNA or RNA.

In a first aspect, the complex may comprise two or more different biological molecules, i.e. the target analyte may be a heteromultimer, e.g. a heterodimer. In this embodiment, the first and second proximity probes comprise different analyte binding domains and may bind simultaneously to two different components of the complex. For example, in a biological complex comprising components A and B, the first proximity probe may bind to component A and the second proximity probe may bind to component B. In this embodiment, the pair of proximity probes comprises first and second analyte binding domains that are different, and that have different binding specificities. The present invention thus provides a method of detecting a target analyte using the probes of the invention, wherein the target analyte is a heteromeric biological complex, wherein the analyte binding domains of the first and second proximity probes are different, and wherein the first and second proximity probes bind to a first and second component of said complex.

In a further aspect, the biological complex may be a homomultimer, i.e. a biological complex comprising two or more copies of the same biological molecule, e.g. a homodimer. In this embodiment, the first and second proximity probes both comprise the same analyte binding domain, and may bind simultaneously to the same region of two separate copies of the analyte in the biological complex. The first and second proximity probes may thus comprise the same analyte binding domain, each of which is conjugated to a different (i.e. a first and second) universal oligonucleotide. Put another way, a first and second universal oligonucleotide may be conjugated separately to the same first and second analyte binding domain, i.e. the first analyte binding domain is also the second analyte binding domain. Thus in this embodiment, the first and second universal conjugates formed in steps (a) and (b) of the present manufacturing methods will both have the same analyte binding domain, and a different (i.e. a first or second) universal oligonucleotide molecule coupled thereto. Appropriate first and second tag oligonucleotides may then be hybridised to the first and second conjugates to form the first and second proximity probes. Thus the present invention provides a method of detecting a target analyte using the probes of the present invention, wherein the target analyte is a homomeric biological complex, wherein the analyte binding domains of the first and second proximity domains are the same, and wherein the first and second proximity probes bind to the same region of the each of the components of the multimer.

The probes of the invention may be used to detect a target analyte in any sample. All biological and clinical samples are included, e.g. any cell or tissue sample of an organism, or any body fluid or preparation derived therefrom, as well as samples such as cell cultures, cell preparations, cell lysates etc. Environmental samples, e.g. soil and water samples or food samples are also included. The samples may be freshly prepared or they may be prior-treated in any convenient way e.g. for storage.

Representative samples thus include any material which may contain a biomolecule, or any other desired or target analyte, including for example foods and allied products, clinical and environmental samples. The sample may be a biological sample, which may contain any viral or cellular material, including all prokaryotic or eukaryotic cells, viruses, bacteriophages, mycoplasmas, protoplasts and organelles. Such biological material may thus comprise all types of mammalian and non-mammalian animal cells, plant cells, algae including bluegreen algae, fungi, bacteria, protozoa etc. Representative samples thus include whole blood and blood-derived products such as plasma, serum and buffy coat, blood cells, urine, faeces, cerebrospinal fluid or any other body fluids (e.g. respiratory secretions, saliva, milk, etc.), tissues, biopsies, cell cultures, cell suspensions, conditioned media or other samples of cell culture constituents, etc. The sample may be pre-treated in any convenient or desired way to prepare for use in the method of the invention, for example by cell lysis or purification, isolation of the analyte, etc.

The universal oligonucleotides may be coupled to the analyte binding domains by any means known in the art, and which may be desired or convenient and may be direct, or indirect e.g. via a linking group. For example, the domains may be associated with one another by covalent linkage (e.g. chemical cross-linking) or by non-covalent association e.g. via streptavidin-biotin based coupling (biotin being provided on one domain particularly the oligonucleotide domain, and streptavidin on the other).

The universal oligonucleotide and analyte binding domain are joined together either directly through a bond or indirectly through a linking group. Where linking groups are employed, such groups may be chosen to provide for covalent attachment of the nucleic acid domain and analyte binding domain through the linking group. The linking group, when present, is in many embodiments biologically inert. In representative embodiments, the linking group is generally at least about 50 Daltons, usually at least about 100 Daltons and may be as large as 1000 Daltons or larger, for example up to 1000000 Daltons if the linking group contains a spacer, but generally will not exceed about 500 Daltons and usually will not exceed about 300 Daltons. Generally, such linkers will comprise a spacer group terminated at either end with a reactive functionality capable of covalently bonding to the nucleic acid domain or analyte binding domain. Spacer groups of interest may include aliphatic and unsaturated hydrocarbon chains, spacers containing heteroatoms such as oxygen (ethers such as polyethylene glycol) or nitrogen (polyamines), peptides, carbohydrates, cyclic or acyclic systems that may possibly contain heteroatoms. Spacer groups may also be comprised of ligands that bind to metals such that the presence of a metal ion coordinates two or more ligands to form a complex. Specific spacer elements include: 1,4-diaminohexane, xylylenediamine, terephthalic acid, 3,6-dioxaoctanedioic acid, ethylenediamine-N,N-diacetic acid, 1,1'-ethylenebis(5-oxo-3-pyrrolidinecarboxylic acid), 4,4'-ethylenedipiperidine.

Potential reactive functionalities include nucleophilic functional groups (amines, alcohols, thiols, hydrazides), electrophilic functional groups (aldehydes, esters, vinyl ketones, epoxides, isocyanates, maleimides), functional groups capable of cycloaddition reactions, forming disulfide bonds, or binding to metals. Specific examples include primary and secondary amines, hydroxamic acids, N-hydroxysuccinimidyl esters, N-hydroxysuccinimidyl carbonates, oxycarbonylimidazoles, nitrophenylesters, trifluoroethyl esters, glycidyl ethers, vinylsulfones, and maleimides.

Specific linker groups that may find use in the subject proximity probes include heterofunctional compounds, such as azidobenzoyl hydrazide, N-[4-(p-azidosalicylamino)butyl]-3'-[2'-pyridyldithio]propionamid), bis-sulfosuccinimidyl suberate, dimethyladipimidate, disuccinimidyltartrate, N-maleimidobutyryloxysuccinimide ester, N-hydroxy sulfosuccinimidyl-4-azidobenzoate, N-succinimidyl [4-azidophenyl]-1,3'-dithiopropionate, N-succinimidyl [4-iodoacetyl]aminobenzoate, glutaraldehyde, and succinimidyl-4-[N-maleimidomethyl]cyclohexane-1-carboxylate, 3-(2-pyridyldithio)propionic acid N-hydroxysuccinimide ester (SPDP), 4-(Nmaleimidomethyl)-cyclohexane-1-carboxylic acid N-hydroxysuccinimide ester (SMCC), and the like.

The nucleic acid domain of the proximity probes may be made up of ribonucleotides and/or deoxyribonucleotides as well as synthetic nucleotide residues that are capable of participating in Watson-Crick type or analogous base pair interactions. Thus, the nucleic acid domain may be DNA or RNA or a combination or any modification thereof e.g. PNA or other derivatives containing non-nucleotide backbones.

As discussed above, it is desired that the proximity probes manufactured via the methods of the present invention may be viewed, treated or used in the same manner as proximity probes known in the art, i.e. proximity probes in which the functional or reactive oligonucleotide domain is directly conjugated to the analyte binding moiety. A comparison of hybridisation probes in a proximity detection assay with conventional proximity probes (i.e. probes known in the art) is provided below. It will be apparent, therefore, that the proximity probes generated by the methods of the present invention may be used in any proximity-based detection assay in the normal way. The tag oligonucleotides may thus be designed to comprise nucleic acid sequences which allow them to interact, directly or indirectly, as may be required.

In one preferred embodiment, the probes of the present invention may be suitable for use in a proximity extension assay. In this embodiment, at least one of the tag oligonucleotides comprises a free 3' end, which is able to hybridise directly or indirectly (i.e. mediated by a further oligonucleotide molecule) to a region of complementarity within the unique domain of the nucleic acid domain of the other proximity probe in a pair when the probes bind to a target analyte in proximity, thereby forming a duplex. A DNA polymerase enzyme may then extend the 3' end of the unique domain using the nucleic acid domain of the other proximity probe (or an oligonucleotide molecule hybridised thereto) as a template for extension by adding dNTPs, thus forming an extension product, which may be, or may be used to provide, a detectable signal, for example as described in U.S. Pat. Nos. 7,306,904 and 6,511,809. The extension product is thus detected to detect the target analyte. The molecule used as a template for extension is linear in this embodiment.

In a particular embodiment, both the first and second tag oligonucleotides may comprise a free 3' end (i.e. the unique domain of the first and second tag oligonucleotides may have free 3' ends). Said free 3' ends may hybridise directly to each other via a region of complementarity, and the 3' end of at least one (or in some embodiments both) tag oligonucleotides may be extended by a DNA polymerase using the nucleic acid domain of the other proximity probe as a template for extension. Thus, in one embodiment, the 3' end of the first tag oligonucleotide may comprise a region of complementarity to the 3' end of the second tag oligonucleotide. As noted above, the regions of complementarity at the ends of the tag oligonucleotides (e.g. at the 3' ends) need not be 100% complementary across their full lengths. Thus, for example, the presence or one or mismatches in the regions of complementarity may be tolerated. The mismatches may be internal in the regions of complementarity and/or they may be at the ends, including at the 3' terminus of the tag oligonucleotides. Thus, in some embodiments the terminal nucleotide(s) (e.g. the terminal 1 to 3 nucleotides) at the 3' ends of the tag oligonucleotides may not be complementary. What is required is that there is a productive hybridisation, which is sufficient to allow the interaction between the tag oligonucleotides e.g. for an extension reaction to take place (e.g. extension of one tag oligonucleotide templated by the other).

The length of the region of complementarity (i.e. the "overlap" between the tag oligonucleotide, or the region of hybridisation) may vary. For example it may lie in the ranges indicated above for hybridisation of universal complement domains to universal oligonucleotides. Alternatively it may be e.g. 5 to 20, 5 to 15, 5 to 12 or 5 to 10 nucleotides long, or from any one of 5, 6 or 7 to any one of 20, 18, 15, 12, 10 or 9 nucleotides long.

Other hybridisation and extension formats are also possible, for example wherein the tag oligonucleotide of one proximity probe has a free 3' end and the other a free 5' end, wherein the tag oligonucleotides (or more particularly portions of the tag oligonucleotides) may hybridise to one another or to a common hybridisation template, or two tag oligonucleotides with free 3' ends (or more particularly portions thereof) hybridise to a common hybridisation template (e.g. an added oligonucleotide molecule), in each case there being at least one 3' end available following hybridisation, which may be extended to form a detectable extension product. Various examples of proximity extension assays are described in WO 2012/104261. However, in such embodiments, the 3' end of the first tag oligonucleotide may comprise a region of complementarity to a region of a third (splint) oligonucleotide present in the sample. The common hybridisation template or third oligonucleotide is preferably linear.

In a further aspect, the probes of the present invention may be suitable for use in a proximity ligation assay. In such an aspect, the tag oligonucleotide of one of the proximity probes may comprise a free 3' end, and the tag oligonucleotide of the other proximity probe may comprise a free 5' end, and said free ends of the respective tag oligonucleotides may comprise regions of complementarity to a third (splint) oligonucleotide in the sample. In other words, the tag oligonucleotides may thus comprise regions of complementarity to a further oligonucleotide molecule (a ligation template) that may template the ligation (directly or indirectly) of the free ends of the tag oligonucleotides. The ends of the tag oligonucleotides may hybridise to said further oligonucleotide such that the 3' free of the first tag oligonucleotide and the 5' free end of the second tag oligonucleotide are directly adjacent to each other, and may thus be ligated directly, or alternatively, the ligation may be indirect, i.e. where the free ends hybridise to the ligation template with a space in between which is filled by a "gap" oligonucleotide such that each free end is ligated to one end of the gap oligonucleotide. In some embodiments, the space in between the free ends may be "filled-in" by extending the free 3' end, e.g. in a polymerase reaction, using the ligation template as an extension template. Once the free 3' end has been extended to be adjacent to the free 5' end, the two ends may be joined by a ligation reaction.

In yet a further aspect, the probes of the present invention may be suitable for use in an in situ proximity ligation assay (in situ PLA). As hereinbefore described, the probes of the present invention may template the circularisation of an oligonucleotide molecule (or a pair of oligonucleotides, e.g. a backbone and splint oligonucleotide molecule). By way of a representative example, the tag oligonucleotides may thus have regions of complementarity, respectively, to (i) the 5' and 3' ends, and (ii) region between said ends, of an added linear oligonucleotide (akin to a "padlock probe"). Upon the addition of an appropriate polymerase, the presence of analyte in the sample may be detected by rolling circle amplification (RCA) of the circularised oligonucleotide, which may optionally be initiated using the 3' end of one of the tag oligonucleotides as a primer. The concatemeric RCA product, which can only be formed when the proximity probes bind in proximity, provides a "surrogate" marker for detection of the analyte.

Other proximity-based detection assays are known in the art, e.g. proximity-hybridisation chain reaction (proximity-HCR), as described in PCT/EP2015/052340. The first tag oligonucleotide may comprise at its free end a region of complementarity to a region of the unique domain of the second tag oligonucleotide that does not lie at the end of the second tag oligonucleotide, i.e. the free end of the second tag oligonucleotide may remain unbound to the first tag oligonucleotide, and may thus be capable of initiating HCR.

It will be seen therefore that the proximity probes of the present invention may be used in any convenient or desired proximity-based detection assay, and the skilled person will thus appreciate that the first and second tag oligonucleotides which are hybridised to the first and second conjugates may be designed to comprise suitable unique domains, depending on the detection assay that is to be performed.

BRIEF DESCRIPTION OF THE DRAWINGS

The present invention may be better understood by reference to the following Examples and Figures, in which:

FIG. 2A and 2B show a comparison of a pair of conventional proximity probes and a pair of hybridisation proximity probes, and provides exemplary oligonucleotide sequences which might be used. A) Conventional proximity probes (the left probe is the functional domain of SEQ ID NO: 5, i.e. with SEQ ID NO: 3 removed, and the right probe is the functional domain of SEQ ID NO: 15 i.e., with SEQ ID NO: 4 removed), comprising a region of complementarity at their 3' ends. B) Proximity probes comprising universal oligonucleotides (the left universal oligonucleotide being SEQ ID NO: 1, and the right univeral oligonucleotide being SEQ ID NO: 2) conjugated to each proximity probe (SEQ ID NOS: 5 and 15,respectively) by its 5' end, and tag oligonucleotides which hybridise to the universal oligonucleotides by a region of complementarity at their 5' ends (SEQ ID NOS: 3 and 4, respectively), and which are able to interact directly via a region of complementarity at their 3' ends.

EXAMPLES

Example 1—Protocol for the Manufacture of Proximity Probes

Ten μl of antibodies (2 μg/μl reconstituted in PBS) were activated at room temperature (RT) for 30 min with a 20-fold molar excess of dibenzylcyclooctyne-NHS ester (DBCO-NHS ester, CLK-A102N, Jena Bioscience; 0.67 μl of a 4 mM solution of DBCO-NHS ester freshly dissolved in DMSO). The DBCO-activated antibodies were purified over a Zeba spin desalting column (7K MWCO, Thermo Scientific) to remove unreacted DBCO-NHS ester. After purification, the activated antibodies were mixed with a 4-fold molar excess of the azide modified oligonucleotides (Universal oligonucleotides 1 and 2) and incubated overnight at 4° C.

Tag oligonucleotides were reconstituted in TE buffer and added to the universal conjugates at 4-fold molar excess. Hybridisation was performed at room temperature in phosphate-buffered saline solution (PBS) for 30 minutes.

Example 2—Detection of a Target Analyte Using a Pair of Proximity Probes

Three separate pairs of proximity probes comprising universal oligonucleotides and three different pairs of tag oligonucleotides (hybridisation probes), and a fourth pair of proximity probes in which the functional domains were conjugated directly to the analyte binding domains, were used in a proximity extension assay to test whether the probes generated using the universal oligonucleotide method were as effective in proximity-based detection assays as conventional proximity probes.

Figure 1A:
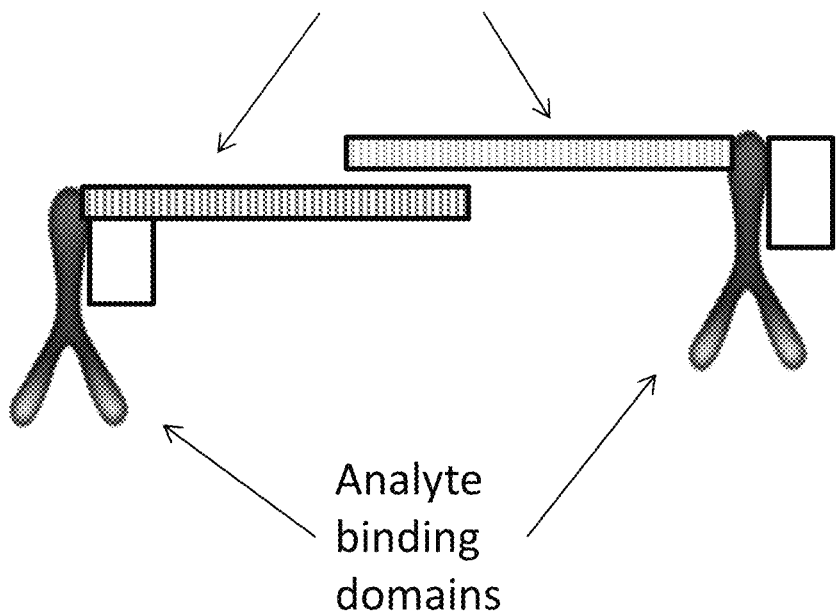
FIG. 1A and 1B show a schematic diagrams comparing a pair of conventional proximity probes with a pair of hybridisation proximity probes. A) Conventional proximity probes, in which the functional domain (the nucleic acid domain) is conjugated directly to the analyte binding domain. B) Proximity probes in which a universal oligonucleotide is conjugated to each proximity probe, and a tag oligonucleotide comprising a universal complement domain hybridises to each to universal oligonucleotide.
Figure 1B:
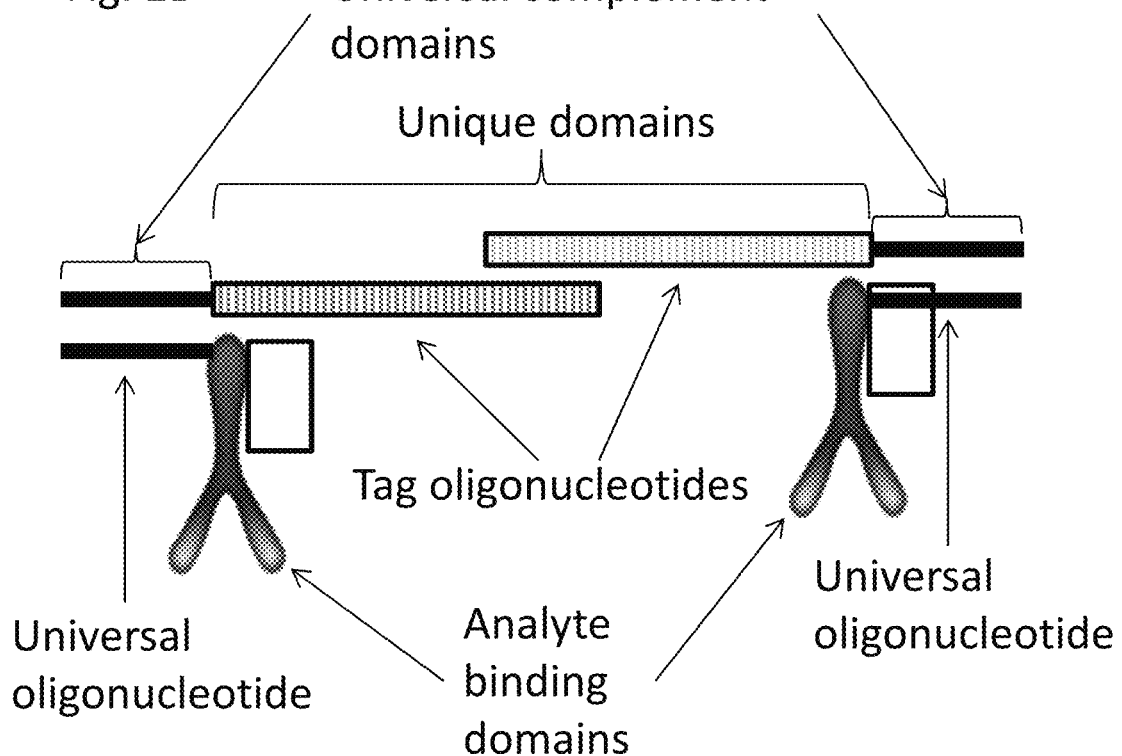
Figure 3A:
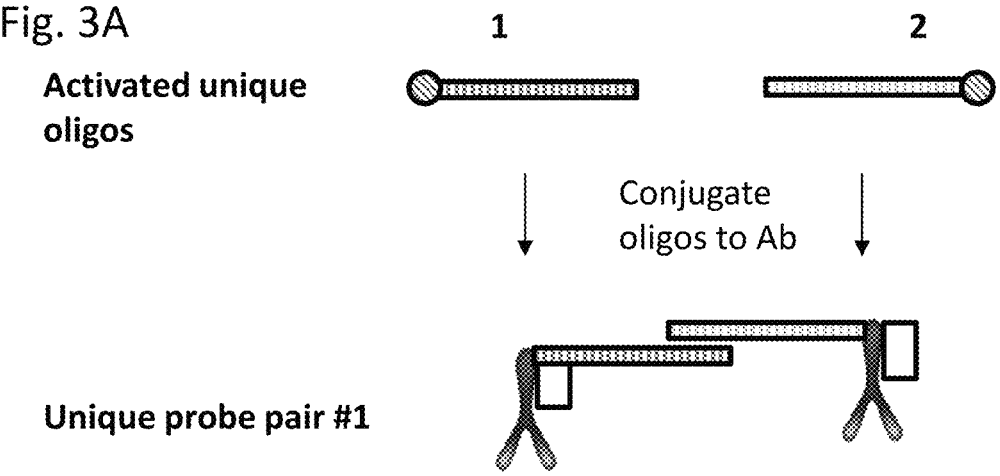
FIG. 3A and 3B show a comparison of the method of manufacture of a pair of conventional proximity probes and a pair of hybridisation proximity probes. A) An oligonucleotide is activated and conjugated to each of the analyte binding domains to form a proximity probe pair. B) Universal oligonucleotides are activated and conjugated to each of the analyte binding domains to form a first and second universal conjugate, and tag oligonucleotides hybridise to each universal oligonucleotide to form a proximity probe pair.
Figure 3B:
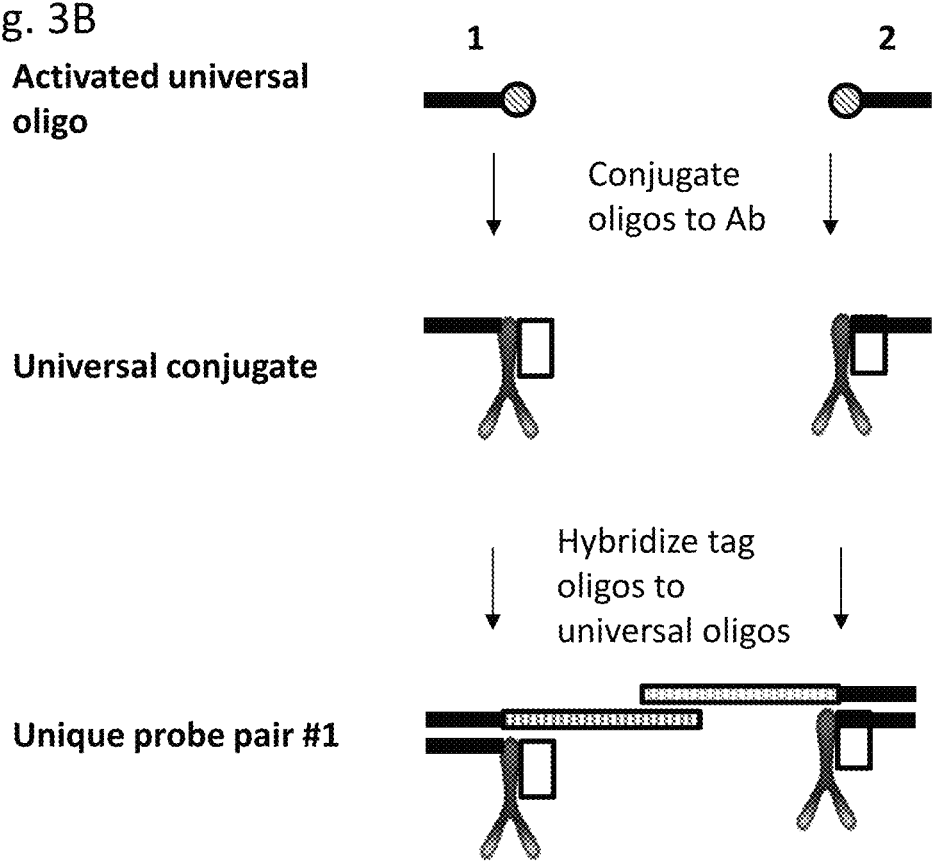
Figure 4A:
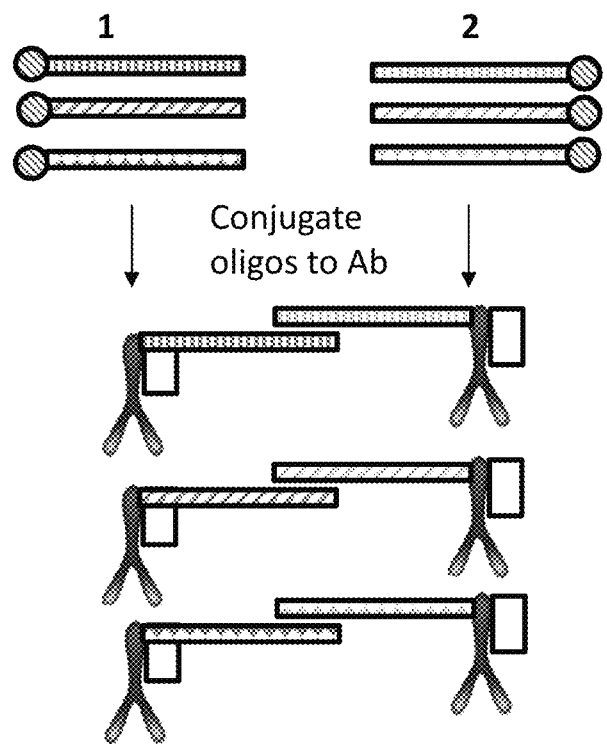
FIG. 4A and 4B show a comparison of a method of manufacturing a plurality of proximity probe pairs via a conventional method and the methods described herein. A) First and second oligonucleotides are activated for each of the proximity probe pairs and conjugated to analyte binding domains. A total of 6 oligonucleotides are activated to produce the 3 proximity probe pairs. B) First and second universal oligonucleotides are activated and conjugated to each of the first and second proximity probes. First and second tag oligonucleotides hybridise to each universal oligonucleotide to form a plurality of proximity probe pairs. A total of 2 oligonucleotides are activated to produce the 3 proximity probe pairs.
Figure 4B:
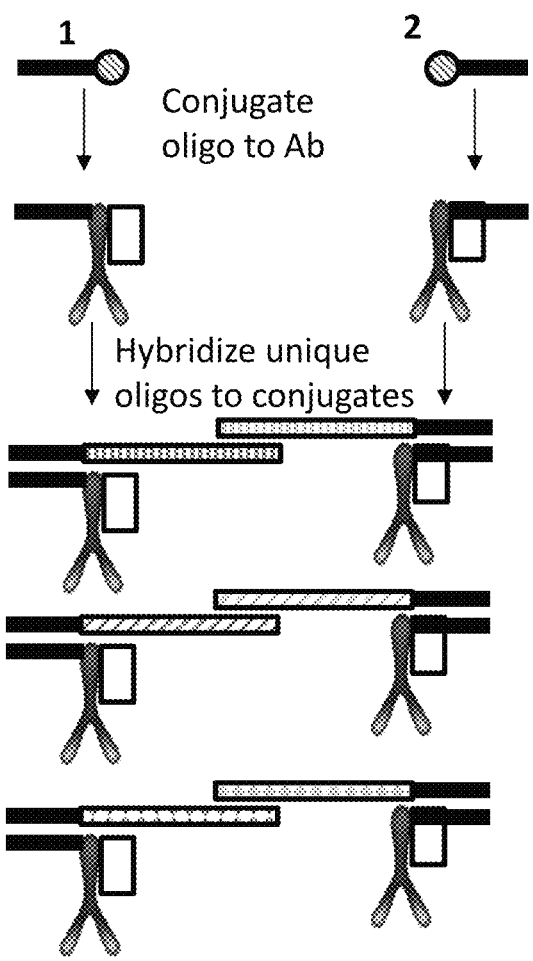
Figure 5A:
FIG. 5A, 5B, and 5C show the detection of Macrophage colony-stimulating factor 1 (CSF-1) in a proximity extension assay using three different pairs of proximity probes comprising different tag oligonucleotide sequences (hybridisation probes), compared with a conventional pair of proximity probes. A) Three separate pairs of proximity probes, each comprising a different pair of tag oligonucleotides but the same analyte binding domains. B) A pair of conventional proximity probes. C) Titration of the detection of CSF-1 using the proximity probes of parts (A) and (B). All of the hybridisation probes tested generated similar levels of signal (hybridisation sequence pair #1-#3), and the proximity-based detection assay has similar sensitivity when conventional proximity probes or hybridisation probes are used (sequence #4 vs sequence #1-#3).
Figure 5A:
Figure 5A:
Figure 5B:
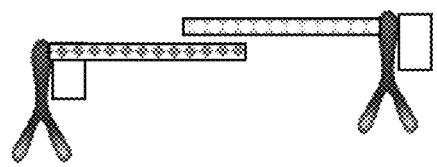
Figure 5C:
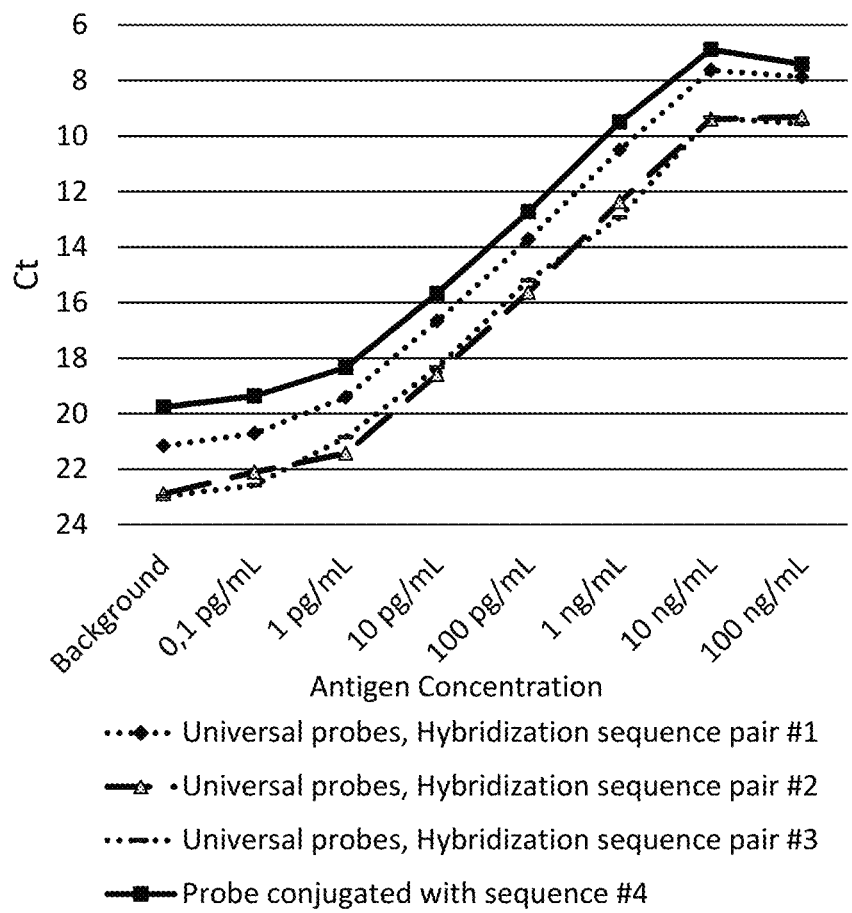

Detection of CSF-1 was performed using the Proseek protocol (Olink AB) according to manufacturer's instructions at a series of different concentrations, in order to obtain a titration curve for each proximity probe pair (see FIG. 5C). Each of the pairs of hybridisation probes were found to be similarly effective in the detection of the target analyte, and each of the hybridisation probes were found to perform similarly to the proximity probes in which the functional nucleic acid molecules were conjugated directly to the analyte binding domains. This demonstrates that hybridisation probes may be useful reagents in proximity-based detection assays.

TABLE 1

Exemplary nucleotide sequences

| SEQ ID NO: | | |
|---|---|---|
| | | Universal oligonucleotide sequences (5'-3') |
| 1 | 1 | TTCTTTAATTGGAGGAGGCC |
| 2 | 2 | CATGGGTTTATTGCCAAGTG |
| | | Universal complement domain sequences (5'-3') |
| 3 | 1' | GGCCTCCTCCAATTAAAGAA |
| 4 | 2' | CACTTGGCAATAAACCCATG |
| | | Example first tag oligonucleotides (5'-3') |
| 5 | Sequence I | GGCCTCCTCCAATTAAAGAACAGGTAGTAGTACGTCTGTTTCACGATGAGACTGGAT |
| 6 | Sequence II | GGCCTCCTCCAATTAAAGAAGGCCTCCTCCAATTAAAGAATCACGATGAGACTGGAT |
| 7 | Sequence III | GGCCTCCTCCAATTAAAGAAGGATCACTCCAACTAGACTATCACGATGAGACTGGAT |
| 8 | Sequence IV | GGCCTCCTCCAATTAAAGAAAGAGTCCACTTCCCATAATGTCACGATGAGACTGGAT |
| 9 | Sequence V | GGCCTCCTCCAATTAAAGAACTACGACTAGGAGATAGATGTCACGATGAGACTGGAT |
| 10 | Sequence VI | GGCCTCCTCCAATTAAAGAACCCTCGTACACAATGGATAATCACGATGAGACTGGAT |
| 11 | Sequence VII | GGCCTCCTCCAATTAAAGAAGACTCCCACTTCTTGTAATGTCACGATGAGACTGGAT |

TABLE 1-continued

Exemplary nucleotide sequences

| SEQ ID NO: | | |
|---|---|---|
| 12 | Sequence VIII | GGCCTCCTCCAATTAAAGAACAGACGGTCAAATCCTCTAATCACGATGAGACTGGAT |
| 13 | Sequence IX | GGCCTCCTCCAATTAAAGAAGAGGTAGCTCACTCCACATGTCACGATGAGACTGGAT |
| 14 | Sequence X | GGCCTCCTCCAATTAAAGAAGTCTAAGATCCTATCACACGTCACGATGAGACTGGAT |
| | | Example second tag oligonucleotides (5'-3') |
| 15 | Sequence I | CACTTGGCAATAAACCCATGGTGCTGCGAGAGTATTATCTTGCACCTTATGCTACCGTGACCTGCGAATCCAGTCT |
| 16 | Sequence II | CACTTGGCAATAAACCCATGGTGAACCGTTATTTGGGTACTGCACCTTATGCTACCGTGACCTGCGAATCCAGTCT |
| 17 | Sequence III | CACTTGGCAATAAACCCATGGTGACAGTGGCAGATATAACTGCACCTTATGCTACCGTGACCTGCGAATCCAGTCT |
| 18 | Sequence IV | CACTTGGCAATAAACCCATGGAACTATGCTGACAGTACCGTGCACCTTATGCTACCGTGACCTGCGAATCCAGTCT |
| 19 | Sequence V | CACTTGGCAATAAACCCATGGCGAGCGTACTATACATAACTGCACCTTATGCTACCGTGACCTGCGAATCCAGTCT |
| 20 | Sequence VI | CACTTGGCAATAAACCCATGGCAGGCAGATCGACCTAGTTTGCACCTTATGCTACCGTGACCTGCGAATCCAGTCT |
| 21 | Sequence VII | CACTTGGCAATAAACCCATGGAGTTTATACTACAGTGCCGTGCACCTTATGCTACCGTGACCTGCGAATCCAGTCT |
| 22 | Sequence VIII | CACTTGGCAATAAACCCATGGTTGCCGTACTAGGGATACTTGCACCTTATGCTACCGTGACCTGCGAATCCAGTCT |
| 23 | Sequence IX | CACTTGGCAATAAACCCATGGCCTGCGAATTAGCGGACATTGCACCTTATGCTACCGTGACCTGCGAATCCAGTCT |
| 24 | Sequence X | CACTTGGCAATAAACCCATGGTTGTTTAGTAAGTGGCACCTGCACCTTATGCTACCGTGACCTGCGAATCCAGTCT |

The invention claimed is:

1. A method of manufacturing a plurality of pairs of proximity probes, wherein each pair of proximity probes comprises a first and a second proximity probe and each pair is capable of binding to a different target analyte, wherein each proximity probe comprises an analyte binding domain and a partially double-stranded nucleic acid domain and each proximity probe of a pair can simultaneously bind to a target analyte, and wherein the nucleic acid domains of a pair of proximity probes are able to interact directly or indirectly upon binding of the pair of proximity probes to their target analyte, said method comprising:
   a. conjugating a first universal oligonucleotide to each of a plurality of first analyte binding moieties, to form a set of first universal conjugates;
   b. conjugating a second universal oligonucleotide to each of a plurality of second analyte binding moieties, to form a set of second universal conjugates;
   c. hybridising to each first universal oligonucleotide of the set of first universal conjugates one of a plurality of different first tag oligonucleotides, each different first tag oligonucleotide comprising a first universal complement domain which is common to all first tag oligonucleotides and which is complementary to the first universal oligonucleotide, and a first unique domain which is unique to each different first tag oligonucleotide and which is not capable of hybridising to a first or second universal oligonucleotide, thereby to form a plurality of first proximity probes;
   d. hybridising to each second universal oligonucleotide of the set of second universal conjugates one of a plurality of different second cognate tag oligonucleotides, each different second tag oligonucleotide comprising a second universal complement domain which is common to all second tag oligonucleotides and which is complementary to the second universal oligonucleotide and a second unique domain which is unique to each different second tag oligonucleotide, and which is not capable of hybridising to a first or second universal oligonucleotide, thereby to form a plurality of second proximity probes;

e. selecting multiple first proximity probes from said plurality of first proximity probes and multiple cognate second proximity probes from said plurality of second proximity probes, thereby to provide a plurality of pairs of proximity probes.

2. The method of claim 1, wherein the first and second universal oligonucleotides are different.

3. The method of claim 1, wherein the first and second universal oligonucleotides are the same.

4. The method of claim 1, wherein said first and second tag oligonucleotides are capable of interacting by hybridisation.

5. The method of claim 4, wherein said first and second tag oligonucleotides comprise free 3' ends.

6. The method of claim 5, wherein said first and second tag oligonucleotides comprise a region of complementarity at their 3' ends.

7. The method of claim 4, wherein said first and or/second tag oligonucleotides may be extended using the cognate tag oligonucleotide as an extension template.

8. The method of claim 1, wherein said first tag oligonucleotide comprises a free 3' end, and wherein said second tag oligonucleotide comprises a free 5' end, wherein said first and second tag oligonucleotides hybridise to a common splint oligonucleotide by their respective free ends.

9. The method of claim 1, wherein the first and second tag oligonucleotides template the circularisation of a circularisable oligonucleotide molecule or a pair of oligonucleotide molecules.

10. The method of claim 9, wherein the first tag oligonucleotide comprises a region of complementarity to the 5' and 3' ends of a first added oligonucleotide molecule, and wherein the second tag oligonucleotide comprises a region of complementarity to a region between said 5' and 3' ends of said first circularisable oligonucleotide or to a second added oligonucleotide.

11. The method of claim 1, wherein the tag oligonucleotide of each first proximity probe may only interact with the tag oligonucleotide of its cognate second proximity probe.

12. The method of claim 1, wherein the tag oligonucleotide of each first proximity probe may interact with the tag oligonucleotide of more than one second proximity probe, preferably with the tag oligonucleotides of all of the second proximity probes.

13. The method of claim 1, wherein the first and/or second tag oligonucleotide of a pair of proximity probes comprises a unique tag sequence that is specific to a particular target analyte, wherein said sequence may be used to identify the particular target analyte present in a sample.

14. The method of claim 1, wherein the first and/or second tag oligonucleotide comprises a universal tag sequence, common to each of the pairs of proximity probes, wherein said sequence may be used to immobilize, analyse, manipulate or amplify the nucleic acid molecule formed as a result of the interaction between the tag oligonucleotides.

15. The method of claim 1, wherein the first and second proximity probes comprise different analyte binding domains and may bind simultaneously to two different regions of the same molecule.

16. The method of claim 1, wherein the first and second proximity probes bind to two separate molecules in a biomolecular complex.

17. The method of claim 16, wherein said first and second proximity probes comprise different analyte binding domains and may bind simultaneously to two separate molecules in a heteromeric complex.

18. The method of claim 17, wherein a first and second proximity probes comprise the same analyte binding domains and may bind simultaneously to two separate molecules in a homomeric complex.

19. The method of claim 1, wherein the analyte binding domains are proteinaceous.

20. The method of claim 19, wherein the analyte binding domains are antibodies.

* * * * *